United States Patent [19]

Powers et al.

[11] Patent Number: 5,180,831
[45] Date of Patent: Jan. 19, 1993

[54] QUATERNARY PYRIDINIUM COMPOUNDS

[75] Inventors: James C. Powers; Sheldon W. May, both of Atlanta; Maria A. Hernandez, Norcross, all of Ga.; Steve Thornton, Raleigh, N.C.; Jan Glinski, New Fairfield, Conn.

[73] Assignee: Georgia Tech Research Corporation, Atlanta, Ga.

[21] Appl. No.: 565,520

[22] Filed: Aug. 10, 1990

[51] Int. Cl.$^5$ .............. C07D 213/65; C07D 213/46; C07D 213/52; C07D 213/53; C07D 401/06
[52] U.S. Cl. ..................... 546/291; 546/292; 546/300; 546/330; 546/268; 546/281; 546/193; 546/331; 546/332; 540/450; 540/484
[58] Field of Search ............... 546/291, 300, 330, 331, 546/332

[56] References Cited

U.S. PATENT DOCUMENTS 5,011,932 4/1991 Rector et al. .................... 546/291

OTHER PUBLICATIONS

Oldiges, H., "Comparative Studies of the Protective Effects of Pyridinium Compounds against Organophosphate Poisoning", *Medical Protection Chem. Warfare Agents SPAP. Symp.* ]1974 pp. 101-108. Pub-Inst. Aerobiol., Fraunhofer-Ges. 1976.

*Primary Examiner*—C. Warren Ivy
*Assistant Examiner*—P. G. Spivack
*Attorney, Agent, or Firm*—Hurt, Richardson, Garner, Todd & Cadenhead

[57] ABSTRACT

Quaternary pyridinium compounds, their use in inhibiting acetylcholinesterase, their roles in the prophylaxis and treatment of organophosphate poisoning, their roles in anticholinesterase therapy and their roles as agents mimicking or opposing the actions of the natural neurotransmitter acetylcholine.

3 Claims, No Drawings

QUATERNARY PYRIDINIUM COMPOUNDS

STATEMENT OF GOVERNMENT INTEREST

This invention was made with Government support under Contract No. DAMD17-85-C-5143 awarded by the U.S. Army Medical Research and Development Command. The Government has certain rights in the invention.

BACKGROUND OF THE INVENTION

1. Field of the Invention

This invention relates to a novel class of quaternary pyridinium compounds useful for selectively inhibiting acetylcholinesterase (AChE) and to their use as nerve agent antidotes and prophylactics. We have found that certain quaternary pyridinium derivatives can offer in vivo protection against the nerve agents Soman (GD) and Tabun (GA) and therefore they can also offer protection against other organophophate poisons. We have also found that certain quaternary pyridinium derivatives can effectively increase the rate of survival of experimental animals exposed to the nerve agents GD and GA and therefore they can also serve as antidotes against other organophosphate poisons. All of the active pyridinium compounds are good AChE inhibitors in vitro and therefore they can also be used to treat conditions where a cholinergic deficit leading to pathology can be ameliorated by administration of an anticholinesterase agent. All of the pyridinium compounds described herein can have additional beneficial effects in living organisms by virtue of their resemblance to the natural neurotransmitter acetylcholine and their ability to act on cholinergic receptors.

2. Description of the Related Art

Development of an effective antidote to organophosphorus (OP) nerve agents has been a goal of medicinal chemists since the development of Tabun in Germany in 1937. OP agents react covalently with the active site serine hydroxyl group of acetylcholinesterase (AChE) to form a stable phosphonyl ester which requires up to 30 days for hydrolysis (Main, A. R. In Biology of Cholinergic Function; Goldberg, A. M., Hanin, I., Eds.; Raven Press: New York, 1976; pp. 269-353, incorporated herein by reference). Excess acetylcholine accumulates and causes severe neurological imbalance, respiratory paralysis, and death (Koelle, G. B. In *The Pharmacological Basis of Therapeutics*; Goodman, L., and Gilman, A., Eds.; MacMillan: New York, 1975; p. 404, incorporated herein by reference). Pyridinium aldoximes (2-PAM and HI-6, see structures below) are currently used in conjunction with an acetylcholine antagonist (atropine) to reactivate the phosphonylated serine hydroxyl group of AChE after poisoning occurs (Leadbeater, L., Inns, R. H., and Rylands, J. M. *Fund. App. Toxicol.* 1985, 5, S225, incorporated herein by reference). This treatment is ineffective against GD and GA because the initially formed enzyme bound alkyl phosphonate esters undergo rapid aging with loss of the alkoxy side chain to form a negatively charged phosphonyl mono ester (Wolthuis, O. L., Berends, F., and Meeter, E., *Fund. Appl. Toxicol.* 1981, 1, 183, incorporated herein by reference). The negative charge on this mono ester repels nucleophiles which are required to dephosphonylate the enzyme.

Other approaches to OP antidotes have dealt with changes in the heteroaromatic ring system in order to improve the reactivation of OP-inhibited acetylcholinesterase (Bedford, C. D., Harris, R. N., III, Howd, R. A., Goff, D. A., Koolpe, G. A., Petesch, M., Koplovitz, I., Sultan, W. E., and Musallam, H. A., *J. Med. Chem.* 1989, 32, 504; Bedford, C. D., Harris, R. N., Howd, R. A., Goff, D. A., Koolpe, G. A., Petesch, M., Miller, A., Nolen, H. W., III, Musallam, H. A., Pick, R. O., Jones, D. E., Koplovitz, I., and Sultan, W. E., *J. Med. Chem.* 1989, 32, 493; Benschop, H. P., Van der Berg, G. R., Van der Hooidonk, C., DeJong, L. P. A., Kientz, C. E., Berends, F., Kepner, L. A., Meeter, E., and Visser, R. P. L. S., *J. Med. Chem.* 1979, 22, 1306; Grifantini, M., Martelli, S., and Stein, M. L., *J. Med. Chem.* 1973, 16, 937, incorporated herein by reference).

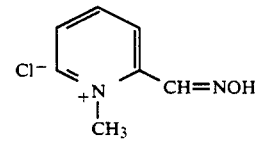

2-PAM Chloride

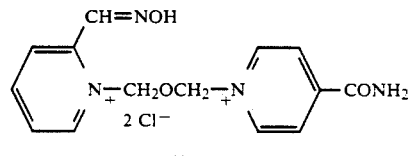

HI-6

Since it is difficult to reactivate aged phosphonylated AChE, prophylactic treatment with AChE inhibitors may be the preferred alternative. AChE is protected from nerve agents by preadministration of an AChE carbamylating agent such as pyridostigmine or physostigmine. These carbamates react covalently with AChE at the active site serine, but the carbamylated enzyme is hydrolyzed quickly to active enzyme (30 min.) while phosphonylated AChE requires several hours or days for regeneration of active AChE (Main, A. R., vide supra). Blocking AChE for a short period of time allows destruction of the OP agent by uncatalyzed hydrolysis or reaction with enzymes such as carboxylesterase or pseudocholinesterase (Harris, L. W., Stitcher, D. L., and Heyl, W. C., *Life Sci.* 1980, 26, 1885, incorporated herein by reference). Unfortunately, physostigmine is very toxic and small doses can be lethal. Furthermore, physostigmine is unstable and would rapidly decompose in the battlefield. Both carbamates are effective only when combined with several other drugs (Heyl, W. C., Harris, L. W., and Stitcher, D. L., *Drug Chem. Toxicol.* 1980, 3, 319, incorporated herein by reference).

Other approaches to prophylaxis against OP poisoning have involved the use of cyclic organophosphates to temporarily block AChE (Ashani, Y., Leader, H., Raveh, L., Bruckstein, R. and Spiegelstein, M., *J. Med. Chem.* 1983, 26, 145, incorporated herein by reference), reduction of AChE levels by inhibition of choline acetyl transferase (Gray, A. P., Platz, R. D., Henderson, T. R., Chang, T. C. P., Takahashi, K. and Dretchen, K. L., *J. Med. Chem.* 1988, 31, 807, incorporated herein by reference), and the use of antimuscarinic α-adrenergic agonists (e.g., clonidine) to block the release of acetylcholine from presynaptic nerve terminals (Buccafusco, J. J. and Aronstam, R. S., *J. Pharmacol. Exp. Ther.* 1986, 239, 43, incorporated herein by reference).

Many oxime, semicarbazone, hydrazone and acyl hydrazone derivatives of 2-formyl-3-hydroxy-1-methylpyridinium chloride described herein incorporate both, a nucleophile to displace the phosphonate from the serine hydroxyl group of AChE and an additional hydrogen bonding group (hydroxyl) to neutralize the negative charge on the aged phosphonate mono ester. In addition, the parent 3-hydroxypyridinium derivatives were converted into various carbamates since these are pyridostigmine analogs and can react covalently with AChE and thus provide protection from OP agents.

DETAILED DESCRIPTION OF THE INVENTION

Aldoxime, hydrazone, semicarbazone and acyl hydrazone derivatives of 2-formyl-1-substituted pyridinium compounds are good inhibitors of acetylcholinesterase (AChE) and can displace a nerve agent from the enzyme active site or protect the latter from attack by a nerve agent. Therefore these structures can be used as antidotes and prophylactics against nerve agents or other organophosphate poisons. Furthermore, it is possible that the carbamates act first as prophylactics against OP poisoning and that the reaction products (3-hydroxy derivatives) act as reactivators of phosphonylated AChE (see below). Herein we describe one instance of this prophylactic/prodrug concept.

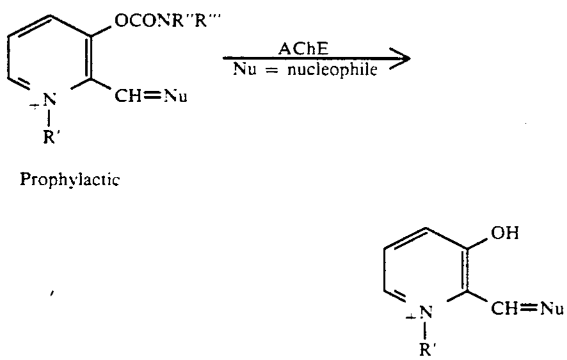

Prophylactic

Reactivator

In addition to their AChE inhibitory properties, these derivatives can act on cholinergic receptors in the nervous system either to mimic or to oppose the effects of the natural neurotransmitter acetylcholine. Therefore these structures can also be used in the treatment of conditions such as Myasthenia Gravis, Alzheimer's disease and adult Down's syndrome where a cholinergic deficit leading to pathology can be ameliorated by administration of a cholinomimetic or an anticholinesterase agent. These structures can also act on the cardiovascular system to produce an antihypertensive effect; they can be useful in the treatment of glaucoma; they can enhance bowel tone and motility.

The novel substituted pyridinium derivatives have the following structural formulas:

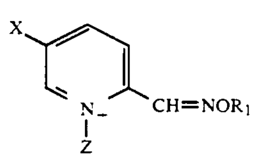

and

-continued 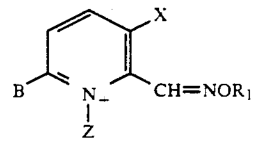 with any counterion to make pharmaceutically acceptable salts, wherein Z is selected from the group consisting of $C_{1-6}$ alkyl, $C_{1-6}$ alkyl with an attached phenyl group, $C_{1-6}$ alkyl with an attached naphtyl group, $C_{1-6}$ alkyl with two attached phenyl groups, $C_{1-6}$ alkyl with an attached phenyl group mono, di, or trisubstituted with J, $C_{1-6}$ alkyl with two attached phenyl groups mono, di, or trisubstituted with J, $C_{1-6}$ alkyl with an attached naphtyl group mono, di, or trisubstituted with J, wherein J is selected from the group consisting of halogen, COOH, OH, CN, $NO_2$, $NH_2$, $C_{1-6}$ alkyl, $C_{1-6}$ alkoxy, $C_{1-6}$ alkylamine, $C_{1-6}$ alkyl-O—CO—, $C_{1-6}$ alkyl-O—CO—NH—, $C_{1-6}$ alkyl-NH—CO—NH—, $C_{1-6}$ alkyl-NH—CO—O—, $C_{1-6}$ alkyl NH—CO—, $(C_{1-6}\ alkyl)_2N$—CO—, wherein X is selected from the group consisting of OH, $C_{1-6}$ alkyl-NH—CO—O—, $(C_{1-6}\ alkyl)_2$-N—CO—O—, $C_{1-6}$ fluoroalkyl-NH—CO—O—, $(C_{1-6}\ fluoroalkyl)_2$-NH—CO—O—, wherein $R_1$ is selected from the group consisting of $C_{1-6}$ alkyl with an attached phenyl group, $C_{1-6}$ alkyl with two attached phenyl groups, $C_{1-6}$ alkyl with an attached phenyl group mono, di, or trisubstituted with K, $C_{1-6}$ alkyl with two attached phenyl groups mono, di, or trisubstituted with K, $C_{1-6}$ alkyl with an attached naphtyl group, $C_{1-6}$ alkyl with an attached naphtyl group mono, di, or trisubstituted with K, $C_{1-6}$ alkyl-T, wherein T is selected from the group consisting of formula (I) and formula (II), Formula I Formula II wherein R', R'', and R''' are selected from the group consisting of H, $C_{1-6}$ alkyl, $C_{1-6}$ fluoroalkyl, $C_{1-6}$ alkyl with an attached phenyl group, $C_{1-6}$ alkyl with an attached phenyl group mono, di, or trisubstituted with K, $C_{1-6}$ fluoroalkyl with an attached phenyl group mono, di, or trisubstituted with K, wherein K is selected from the group consisting of halogen, COOH, OH, CN, $NO_2$, $NH_2$, $C_{1-6}$ alkyl, $C_{1-6}$ alkoxy, $C_{1-6}$ alkylamine, $C_{1-6}$ alkyl-O—CO—, $C_{1-6}$ alkyl-O—CO—NH—, $C_{1-6}$ alkyl-NH—CO—NH—, $C_{1-6}$ alkyl-NH—CO—O—, $C_{1-6}$ alkyl NH—CO—, $(C_{1-6}\ alkyl)_2N$—CO—, wherein B is selected from the group consisting of H, $C_{1-6}$ alkyl.

Alternatively the novel quaternary pyridinium compounds are represented by the following structural formulas:

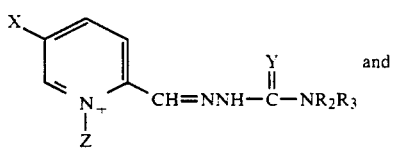

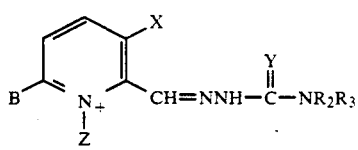

with any counterion to make pharmaceutically acceptable salts, wherein

Y is O or S, wherein $R_2$ is selected from the group consisting of H, $C_{1-6}$ alkyl, phenyl, $C_{1-6}$ alkyl with an attached phenyl group, $C_{1-6}$ alkyl with an attached phenyl group mono, di, or trisubstituted with K, $C_{1-6}$ alkyl with an attached naphtyl group, $C_{1-6}$ alkyl with an attached naphtyl group mono, di, or trisubstituted with K, wherein $R_3$ is selected from the group consisting of H, $C_{1-6}$ alkyl, phenyl, $C_{1-6}$ alkyl with an attached phenyl group, $C_{1-6}$ alkyl with an attached phenyl group mono, di, or trisubstituted with K.

Alternatively the novel quaternary pyridinium compounds are represented by the following structural formulas:

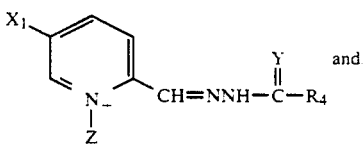

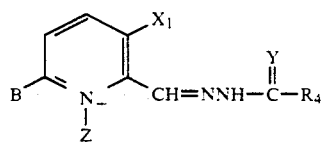

with any counterion to make pharmaceutically acceptable salts, wherein $X_1$ is selected from the group consisting of H, OH, $C_{1-6}$ alkyl-NH—CO—O—, $(C_{1-6}$ alkyl$)_2$-N—CO—O—, $C_{1-6}$ fluoroalkyl-NH—CO—O—, $(C_{1-6}$ fluoroalkyl$)_2$-NH—CO—O—, wherein $R_4$ is selected from the group consisting of $C_{1-6}$ alkyl with a pyridinium ring attached through nitrogen, $C_{1-6}$ alkyl with a pyridinium ring attached through nitrogen and mono, di, or trisubstituted with K, $C_{1-6}$ alkyl with a quinolinium ring attached through nitrogen and mono, di, or trisubstituted with K, $C_{1-6}$ alkyl with an isoquinolinium ring attached through nitrogen and mono, di, or trisubstituted with K, $C_{1-6}$ alkyl-T, wherein T is selected from the group consisting of formula (I) and formula (II),

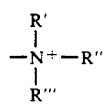

Formula I

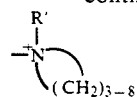

Formula II wherein R', R'', and R''' are selected from the group consisting of H, $C_{1-6}$ alkyl, $C_{1-6}$ fluoroalkyl, $C_{1-6}$ alkyl with an attached phenyl group, $C_{1-6}$ alkyl with an attached phenyl group mono, di, or trisubstituted with K, $C_{1-6}$ fluoroalkyl with an attached phenyl group mono, di, or trisubstituted with K, wherein K is selected from the group consisting of halogen, COOH, OH, CN, $NO_2$, $NH_2$, $C_{1-6}$ alkyl, $C_{1-6}$ alkoxy, $C_{1-6}$ alkylamine, $C_{1-6}$ alkyl-O—CO—, $C_{1-6}$ alkyl-O—CO—NH—, $C_{1-6}$ alkyl-NH—CO—NH—, $C_{1-6}$ alkyl-NH—CO—O—, $C_{1-6}$ alkyl NH—CO—, $(C_{1-6}$ alkyl$)_2$N—CO—.

Alternatively the novel quaternary pyridinium compounds are represented by the following structural formulas:

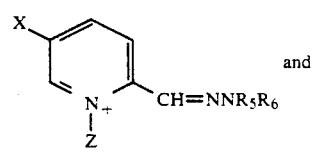

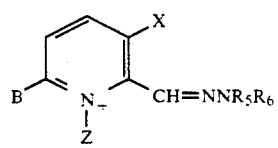

with any counterion to make pharmaceutically acceptable salts, wherein $R_5$ is selected from the group consisting of $C_{1-6}$ alkyl, phenyl, $C_{1-6}$ alkyl with an attached phenyl group, $C_{1-6}$ alkyl with an attached phenyl group mono, di, or trisubstituted with K, $C_{1-6}$ alkyl with an attached naphtyl group, $C_{1-6}$ alkyl with an attached naphtyl group mono, di, or trisubstituted with K, wherein $R_6$ is selected from the group consisting of H, $C_{1-6}$ alkyl, phenyl, $C_{1-6}$ alkyl with an attached phenyl group, $C_{1-6}$ alkyl with an attached phenyl group mono, di, or trisubstituted with K.

Alternatively the novel quaternary pyridinium compounds are represented by the following structural formulas:

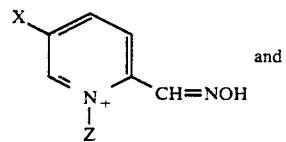

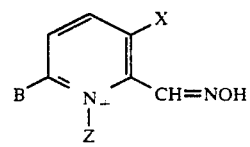

with any counterion to make pharmaceutically acceptable salts.

Alternatively the novel quaternary pyridinium compounds are represented by the following structural formula:

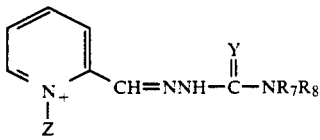

with any counterion to make pharmaceutically acceptable salts, wherein $R_7$ is selected from the group consisting of $C_{1-6}$ alkyl, phenyl, $C_{1-6}$ alkyl with an attached phenyl group, $C_{1-6}$ alkyl with an attached phenyl group mono, di, or trisubstituted with K, $C_{1-6}$ alkyl with an attached naphtyl group, $C_{1-6}$ alkyl with an attached naphtyl group mono, di, or trisubstituted with K, —CO—$C_{1-6}$ alkyl, —CO—$C_{1-6}$ alkyl with an attached phenyl group mono, di, or trisubstituted with K, wherein $R_8$ is selected from the group consisting of H, $C_{1-6}$ alkyl, phenyl, $C_{1-6}$ alkyl with an attached phenyl group, $C_{1-6}$ alkyl with an attached phenyl group mono, di, or trisubstituted with K.

Alternatively the novel quaternary pyridinium compounds are represented by the following structural formula:

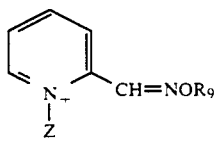

with any counterion to make pharmaceutically acceptable salts, wherein $R_9$ is selected from the group consisting of $C_{1-6}$ alkyl with an attached phenyl group, $C_{1-6}$ alkyl with two attached phenyl groups, $C_{1-6}$ alkyl with an attached phenyl group mono, di, or trisubstituted with K, $C_{1-6}$ alkyl with two attached phenyl groups mono, di, or trisubstituted with K, $C_{1-6}$ alkyl with an attached naphtyl group, $C_{1-6}$ alkyl with an attached naphtyl group mono, di, or trisubstituted with K.

The following compounds are representative of the invention:

O-Benzyl-N-(1-methyl-2-pyridinemethylene) hydroxylamine chloride (1a).
O-(Diphenylmethyl)-N-(1-methyl-2-pyridinemethylene) hydroxylamine chloride.
O-(p-Chlorobenzyl)-N-(1-methyl-2-pyridinemethylene) hydroxylamine chloride.
O-(p-Methoxybenzyl)-N-(1-methyl-2-pyridinemethylene) hydroxylamine chloride.
O-(1-Naphtylmethyl)-N-(1-methyl-2-pyridinemethylene) hydroxylamine chloride.
O-(2-Methyl-1-naphtylmethyl)-N-(1-methyl-2-pyridinemethylene) hydroxylamine chloride.
O-(2,3,4-Trimethoxybenzyl)-N-(1-methyl-2-pyridinemethylene) hydroxylamine chloride.
O-(3,3-Diphenylpropyl)-N-(1-methyl-2-pyridinemethylene) hydroxylamine chloride.
O-Benzyl-N-(3-hydroxy-1-methyl-2-pyridinemethylene) hydroxylamine chloride (1b).
O-(1-Naphtylmethyl)-N-(3-hydroxy-1-methyl-2-pyridinemethylene) hydroxylamine chloride.
O-(2-Methyl-1-naphtylmethyl)-N-(3-hydroxy-1-methyl-2-pyridinemethylene) hydroxylamine chloride.
O-(2,3,4-Trimethoxybenzyl)-N-(3-hydroxy-1-methyl-2-pyridinemethylene) hydroxylamine chloride.
O-(3,3-Diphenylpropyl)-N-(3-hydroxy-1-methyl-2-pyridinemethylene) hydroxylamine chloride.
O-(1-Naphtylmethyl)-N-(1,6-dimethyl-3-hydroxy-2-pyridinemethylene) hydroxylamine chloride.
O-(2-Methyl-1-naphtylmethyl)-N-(1,6-dimethyl-3-hydroxy-2-pyridinemethylene) hydroxylamine chloride.
O-Methyl-N-(3-hydroxy-1-methyl-2-pyridinemethylene) hydroxylamine chloride (1c).
O-Methyl-N-(1,6-dimethyl-3-hydroxy-2-pyridinemethylene) hydroxylamine chloride.
O-[2-(1-Methyl-1-piperidinium]ethyl]-N-(3-hydroxy-1-methyl-2-pyridinemethylene) hydroxylamine dichloride.
O-[2-(Trimethylammonium)ethyl]-N-(3-hydroxy-1-methyl-2-pyridinemethylene) hydroxylamine dichloride.
O-(p-Chlorobenzyl)-N-(3-hydroxy-1-methyl-2-pyridinemethylene) hydroxylamine chloride (1d).
O-(p-Cyanobenzyl)-N-(3-hydroxy-1-methyl-2-pyridinemethylene) hydroxylamine chloride.
O-(2-Hydroxy-4-nitrobenzyl)-N-(3-hydroxy-1-methyl-2-pyridinemethylene) hydroxylamine chloride.
O-(p-Carboxybenzyl)-N-(3-hydroxy-1-methyl-2-pyridinemethylene) hydroxylamine chloride.
O-(p-Chlorobenzyl)-N-(1,6-dimethyl-3-hydroxy-2-pyridinemethylene) hydroxylamine chloride.
O-(p-Cyanobenzyl)-N-(1,6-dimethyl-3-hydroxy-2-pyridinemethylene) hydroxylamine chloride.
O-(2-Hydroxy-4-nitrobenzyl)-N-(1,6-dimethyl-3-hydroxy-2-pyridinemethylene) hydroxylamine chloride.
O-(p-Methoxybenzyl)-N-(3-hydroxy-1-methyl-2-pyridinemethylene) hydroxylamine chloride (1e).
O-(p-Dimethylaminocarbonyloxy benzyl)-N-(3-hydroxy-1-methyl-2-pyridinemethylene) hydroxylamine chloride.
O-(p-Propylaminocarbonyl benzyl)-N-(3-hydroxy-1-methyl-2-pyridinemethylene) hydroxylamine chloride.
O-(p-Ethoxycarbonyl benzyl)-N-(3-hydroxy-1-methyl-2-pyridinemethylene) hydroxylamine chloride.
O-(p-Methoxybenzyl)-N-(1,6-dimethyl-3-hydroxy-2-pyridinemethylene) hydroxylamine chloride.
O-(p-Dimethylaminocarbonyloxy benzyl)-N-(1,6-dimethyl-3-hydroxy-2-pyridinemethylene) hydroxylamine chloride.
O-(p-Propylaminocarbonyl benzyl)-N-(1,6-dimethyl-3-hydroxy-2-pyridinemethylene) hydroxylamine chloride.
O-Benzyl-N-[3-(N',N'-dimethylcarbamoyl)hydroxy-1-methyl-2-pyridinemethylene]hydroxylamine chloride (2a).
O-[2-(1-Methyl-1-piperidinium)ethyl]-N-[3-(N',N'-dimethylcarbamoyl)hydroxy-1-methyl-2-pyridinemethylene]hydroxylamine dichloride.
O-[2-(Trimethylammonium)ethyl]-N-[3-(N',N'-dimethylcarbamoyl)hydroxy-1-methyl-2-pyridinemethylene]hydroxylamine dichloride.
O-Benzyl-N-[3-(N',N'-diethylcarbamoyl)hydroxy-1-methyl-2-pyridinemethylene]hydroxylamine chloride.

O-Benzyl-N-[3-(N',N'-difluoroethylcarbamoyl)hydroxy-1-methyl-2-pyridinemethylene]hydroxylamine chloride.

O-Diphenylmethyl-N-(3-hydroxy-1-methyl-2-pyridinemethylene) hydroxylamine iodide.

O-Benzyl-N-[3-(N',N'-dimethylcarbamoyl)hydroxy-1,6-dimethyl-2-pyridinemethylene]hydroxylamine chloride.

O-Benzyl-N-[3-(N',N'-diethylcarbamoyl)hydroxy-1,6-dimethyl-2-pyridinemethylene]hydroxylamine chloride.

O-Benzyl-N-[3-(N',N'-difluoroethylcarbamoyl)hydroxy-1,6-dimethyl-2-pyridinemethylene]hydroxylamine chloride.

O-(Diphenylmethyl)-N-[3-(N',N'-dimethylcarbamoyl)hydroxy-1-methyl-2-pyridinemethylene]hydroxylamine chloride (2b).

O-(Diphenylmethyl)-N-[3-(N'-isopropylcarbamoyl)hydroxy-1-methyl-2-pyridinemethylene]hydroxylamine chloride.

O-(Diphenylmethyl)-N-[3-[N'-(2-fluoroethyl)carbamoyl]hydroxy-1-methyl-2-pyridinemethylene]hydroxylamine chloride.

O-(Diphenylmethyl)-N-[3-(N',N'-dimethylcarbamoyl)hydroxy-1,6-dimethyl-2-pyridinemethylene]hydroxylamine chloride.

O-(Diphenylmethyl)-N-[1,6-dimethyl-3-(N'-isopropylcarbamoyl)hydroxy-2-pyridinemethylene]hydroxylamine chloride.

O-(Diphenylmethyl)-N-[3-[N'-(2-fluoroethyl)carbamoyl]hydroxy-1,6-dimethyl-2-pyridinemethylene]hydroxylamine chloride.

O-(p-Methoxybenzyl)-N-[3-(N',N'-dimethylcarbamoyl)hydroxy-1-methyl-2-pyridinemethylene]hydroxylamine chloride (2c).

O-(p-Methoxybenzyl)-N-[3-(N',N'-dimethylcarbamoyl)hydroxy-1-ethyl-2-pyridinemethylene]hydroxylamine chloride.

O-(p-Methoxybenzyl)-N-[3-(N',N'-dimethylcarbamoyl)hydroxy-1-benzyl-2-pyridinemethylene]hydroxylamine bromide.

O-(p-Methoxybenzyl)-N-[3-(N',N'-dimethylcarbamoyl)hydroxy-1,6-dimethyl-2-pyridinemethylene]hydroxylamine chloride.

O-(p-Methoxybenzyl)-N-[3-(N',N'-dimethylcarbamoyl)hydroxy-1-ethyl-6-methyl-2-pyridinemethylene]hydroxylamine chloride.

O-(p-Methoxybenzyl)-N-[3-(N',N'-dimethylcarbamoyl)hydroxy-1-benzyl-6-methyl-2-pyridinemethylene]hydroxylamine bromide.

O-(p-Methoxybenzyl)-N-[3-(N',N'-dimethylcarbamoyl)hydroxy-1-(1-naphtylmethyl)-2-pyridinemethylene]hydroxylamine chloride.

O-(p-Methoxybenzyl)-N-[3-(N',N'-dimethylcarbamoyl)hydroxy-1-(2-methyl-1-naphtylmethyl)-2-pyridinemethylene]hydroxylamine chloride.

O-(p-Methoxybenzyl)-N-[3-(N',N'-dimethylcarbamoyl)hydroxy-1-diphenylmethyl-2-pyridinemethylene]hydroxylamine chloride.

O-(p-Methoxybenzyl)-N-[3-(N',N'-dimethylcarbamoyl)hydroxy-1-(2-hydroxy-4-nitro benzyl)-2-pyridinemethylene]hydroxylamine chloride.

O-(p-Methoxybenzyl)-N-[3-(N',N'-dimethylcarbamoyl)hydroxy-1-(p-carboxy benzyl)-2-pyridinemethylene]hydroxylamine chloride.

O-(p-Methoxybenzyl)-N-[3-(N',N'-dimethylcarbamoyl)hydroxy-1-(p-cyanobenzyl)-2-pyridinemethylene]hydroxylamine chloride.

N-[5-(N',N'-Dimethylcarbamoyl)hydroxy-1-methyl-2-pyridinemethylene]hydroxylamine chloride (2d).

N-[3-(N',N'-Dimethylcarbamoyl)hydroxy-1-methyl-2-pyridinemethylene]hydroxylamine chloride.

N-[3-(N',N'-Dimethylcarbamoyl)hydroxy-1,6-dimethyl-2-pyridinemethylene]hydroxylamine chloride.

O-(1-Naphtylmethyl)-N-(5-hydroxy-1-methyl-2-pyridinemethylene) hydroxylamine chloride.

O-(2-Methyl-1-naphtylmethyl)-N-(5-hydroxy-1-methyl-2-pyridinemethylene) hydroxylamine chloride.

O-(2,3,4-Trimethoxybenzyl)-N-(5-hydroxy-1-methyl-2-pyridinemethylene) hydroxylamine chloride.

O-(3,3-Diphenylpropyl)-N-(5-hydroxy-1-methyl-2-pyridinemethylene) hydroxylamine chloride.

O-Methyl-N-(5-hydroxy-1-methyl-2-pyridinemethylene) hydroxylamine chloride.

O-(p-Chlorobenzyl)-N-(5-hydroxy-1-methyl-2-pyridinemethylene) hydroxylamine chloride.

O-(p-Cyanobenzyl)-N-(5-hydroxy-1-methyl-2-pyridinemethylene) hydroxylamine chloride.

O-(2-Hydroxy-4-nitro benzyl)-N-(5-hydroxy-1-methyl-2-pyridinemethylene) hydroxylamine chloride.

O-(p-Carboxy benzyl)-N-(5-hydroxy-1-methyl-2-pyridinemethylene) hydroxylamine chloride.

O-(p-Methoxybenzyl)-N-(5-hydroxy-1-methyl-2-pyridinemethylene) hydroxylamine chloride.

O-(p-Dimethylaminocarbonyloxy benzyl)-N-(5-hydroxy-1-methyl-2-pyridinemethylene) hydroxylamine chloride.

O-(p-Propylaminocarbonyl benzyl)-N-(5-hydroxy-1-methyl-2-pyridinemethylene) hydroxylamine chloride.

O-(p-Ethoxycarbonyl benzyl)-N-(5-hydroxy-1-methyl-2-pyridinemethylene) hydroxylamine chloride.

O-Benzyl-N-[5-(N',N'-dimethylcarbamoyl)hydroxy-1-methyl-2-pyridinemethylene]hydroxylamine chloride.

O-Benzyl-N-[5-(N',N'-diethylcarbamoyl)hydroxy-1-methyl-2-pyridinemethylene]hydroxylamine chloride.

O-Benzyl-N-[5-(N',N'-difluoroethylcarbamoyl)hydroxy-1-methyl-2-pyridinemethylene]hydroxylamine chloride.

O-(Diphenylmethyl)-N-[5-(N'-isopropylcarbamoyl)hydroxy-1-methyl-2-pyridinemethylene]hydroxylamine chloride.

O-(Diphenylmethyl)-N-[5-[N'-(2-fluoroethyl)carbamoyl]hydroxy-1-methyl-2-pyridinemethylene]hydroxylamine chloride.

O-(p-Methoxybenzyl)-N-[5-(N',N'-dimethylcarbamoyl)hydroxy-1-methyl-2-pyridinemethylene]hydroxylamine chloride.

O-(p-Methoxybenzyl)-N-[5-(N',N'-dimethylcarbamoyl)hydroxy-1-ethyl-2-pyridinemethylene]hydroxylamine chloride.

O-(p-Methoxybenzyl)-N-[5-(N',N'-dimethylcarbamoyl)hydroxy-1-benzyl-2-pyridinemethylene]hydroxylamine bromide.

O-(p-Methoxybenzyl)-N-[5-(N',N'-dimethylcarbamoyl)hydroxy-1-(1-naphtylmethyl)-2-pyridinemethylene]hydroxylamine chloride.

O-(p-Methoxybenzyl)-N-[5-(N',N'-dimethylcarbamoyl)hydroxy-1-(2-methyl-1-naphtylmethyl)-2-pyridinemethylene]hydroxylamine chloride.

O-(p-Methoxybenzyl)-N-[5-(N',N'-dimethylcarbamoyl)hydroxy-1-diphenylmethyl-2-pyridinemethylene]hydroxylamine chloride.

O-(p-Methoxybenzyl)-N-[5-(N',N'-dimethylcarbamoyl)hydroxy-1-(2-hydroxy-4-nitro benzyl)-2-pyridinemethylene]hydroxylamine chloride.

O-(p-Methoxybenzyl)-N-[5-(N',N'-dimethylcarbamoyl)hydroxy-1-(p-carboxy benzyl)-2-pyridinemethylene]hydroxylamine chloride.

O-(p-Methoxybenzyl)-N-[5-(N',N'-dimethylcarbamoyl)hydroxy-1-(p-cyanobenzyl)-2-pyridinemethylene]hydroxylamine chloride.

O-Benzyl-N-(1-benzyl-3-hydroxy-2-pyridinemethylene) hydroxylamine bromide.

O-Benzyl-N-(1-benzyl-5-hydroxy-2-pyridinemethylene) hydroxylamine bromide.

2-[[(Aminocarbonyl)hydrazono]methyl]-3-hydroxy-1-methyl pyridinium chloride (3a).

2-[[(Aminocarbonyl)hydrazono]methyl]-5-hydroxy-1-methyl pyridinium chloride.

2-[[(Aminothiocarbonyl)hydrazono]methyl]-3-hydroxy-1-methyl pyridinium chloride.

2-[[(Aminothiocarbonyl)hydrazono]methyl]-5-hydroxy-1-methyl pyridinium chloride.

2-Hydrazonomethyl-3-hydroxy-1-methyl pyridinium chloride.

2-Hydrazonomethyl-3-hydroxy-1,6-dimethyl pyridinium chloride.

2-Hydrazonomethyl-5-hydroxy-1-methyl pyridinium chloride.

1-Methyl-2-(3-hydroxy-1-methyl-2-pyridinemethylene) hydrazine chloride.

1-Methyl-1-phenyl-2-(3-hydroxy-1-methyl-2-pyridinemethylene) hydrazine chloride.

1,1-Diphenyl-2-(3-hydroxy-1-methyl-2-pyridinemethylene) hydrazine chloride.

1-(2,4-Dinitrophenyl)-2-(3-hydroxy-1-methyl-2-pyridinemethylene) hydrazine chloride.

1-Naphtyl-2-(3-hydroxy-1-methyl-2-pyridinemethylene) hydrazine chloride.

1-Methyl-2-(5-hydroxy-1-methyl-2-pyridinemethylene) hydrazine chloride.

1-Methyl-1-phenyl-2-(5-hydroxy-1-methyl-2-pyridinemethylene) hydrazine chloride.

1,1-Diphenyl-2-(5-hydroxy-1-methyl-2-pyridinemethylene) hydrazine chloride.

1-(2,4-Dinitrophenyl)-2-(5-hydroxy-1-methyl-2-pyridinemethylene) hydrazine chloride.

1-Naphtyl-2-(5-hydroxy-1-methyl-2-pyridinemethylene) hydrazine chloride.

1Methyl-2-(1,6-dimethyl-3-hydroxy-2-pyridinemethylene) hydrazine chloride.

1-Methyl-1-phenyl-2-(1,6-dimethyl-3-hydroxy-2-pyridinemethylene) hydrazine chloride.

1,1-Diphenyl-2-(1,6-dimethyl-3-hydroxy-2-pyridinemethylene) hydrazine chloride.

3-Hydroxy-1-methyl-2-[[(N-phenylaminocarbonyl)hydrazono]methyl]pyridinium chloride (3b).

1,6-Dimethyl-3-hydroxy-2-[[(N-phenylaminocarbonyl)hydrazono]methyl]pyridinium chloride.

5-Hydroxy-1-methyl-2-[[(N-phenylaminocarbonyl)hydrazono]methyl]pyridinium chloride.

3-Hydroxy-1-methyl-2-[[(N-phenylaminothiocarbonyl)hydrazono]methyl]pyridinium chloride.

2-[[(N,N-Diphenylaminocarbonyl)hydrazono]methyl]-3-hydroxy-1-methyl pyridinium chloride.

1,6-Dimethyl-3-hydroxy-2-[[(N-phenylaminothiocarbonyl)hydrazono]methyl]pyridinium chloride.

1,6-Dimethyl-2-[[(N,N -diphenylaminocarbonyl)hydrazono]methyl]-3-hydroxy pyridinium chloride.

2-[[(N,N-Dimethylaminothiocarbonyl)hydrazono]methyl]3-hydroxy-1-methyl pyridinium chloride.

2-[[(N-Ethylaminothiocarbonyl)hydrazono]methyl]-3-hydroxy-1-methyl pyridinium chloride.

3-Hydroxy-1-methyl-2-[[(N-naphtylaminocarbonyl)hydrazono]methyl]pyridinium chloride.

2-[[[N-(1-Chloro-2-naphtyl)amino carbonyl]hydrazono]methyl]-3-hydroxy-1-methyl pyridinium chloride.

5-Hydroxy-1-methyl-2-[[(N-phenylaminothiocarbonyl)hydrazono]methyl]pyridinium chloride.

2-[[(N,N-Diphenylaminocarbonyl)hydrazono]methyl]-5-hydroxy-1-methyl pyridinium chloride.

2-[[(N,N-Dimethylaminothiocarbonyl)hydrazono]methyl]-5-hydroxy-1-methyl pyridinium chloride.

2-[[(N-Ethylaminothiocarbonyl)hydrazono]methyl]-5-hydroxy-1-methyl pyridinium chloride.

5-Hydroxy-1-methyl-2-[[(N-naphtylaminocarbonyl)hydrazono]methyl]pyridinium chloride.

2-[[[N-(1-Chloro-2-naphtyl)amino carbonyl]hydrazono]methyl]-5-hydroxy-1-methyl pyridinium chloride.

1-Methyl-2-[[(N-phenylaminocarbonyl)hydrazono]methyl]pyridinium chloride (3d).

2-[[(Aminocarbonyl)hydrazono]methyl]-3-(N,N-dimethylcarbamoyl)hydroxy-1-methyl pyridinium chloride (4a).

2-[[(Aminocarbonyl)hydrazono]methyl]-3-(N,N-dimethylcarbamoyl)hydroxy-1,6-dimethyl pyridinium chloride.

2-[[(Aminocarbonyl)hydrazono]methyl]-5-(N,N-dimethylcarbamoyl)hydroxy-1-methyl pyridinium chloride 3-(N,N-Dimethylcarbamoyl)hydroxy-1-methyl-2-[[(N-phenylaminocarbonyl) hydrazono]methyl]-pyridinium chloride (4b).

5-(N,N-Dimethylcarbamoyl)hydroxy-1-methyl-2-[[(N-phenylaminocarbonyl) hydrazono]methyl]-pyridinium chloride.

2-(3-Hydroxy-1-methyl-2-pyridinemethylene)-1-[2-(1-pyridinium)acetyl]hydrazine dichloride (5a).

2-(1,6-Dimethyl-3-hydroxy-2-pyridinemethylene)-1-[2-(1-pyridinium)acetyl]hydrazine dichloride.

2-(5-Hydroxy-1-methyl-2-pyridinemethylene)-1-[2-(1-pyridinium)acetyl]hydrazine dichloride.

2-(3-Hydroxy-1-methyl-2-pyridinemethylene)-1-[2-(trimethylammonium)acetyl]hydrazine dichloride.

1-[2-(4-Chloro-1-pyridinium)acetyl]-2-(3-hydroxy-1-methyl-2-pyridinemethylene) hydrazine dichloride.

2-(1,6-Dimethyl-3-hydroxy-2-pyridinemethylene)-1-[2-(trimethylammonium)acetyl]hydrazine dichloride.

2-(1,6-Dimethyl-3-hydroxy-2-pyridinemethylene)-1-[2-(4-chloro-1-pyridinium)acetyl]hydrazine dichloride.

1-[2-(3-Carboxy-1-isoquinolinium)acetyl]-2-(3-hydroxy-1-methyl-2-pyridinemethylene) hydrazine dichloride.

1-[2-(2-Carboxy-4-methoxy-1-quinolinium)acetyl]-2-(3-hydroxy-1-methyl-2-pyridinemethylene) hydrazine dichloride.

2-(3-Hydroxy-1-methyl-2-pyridinemethylene)-1-[2-(3-hydroxy-1-pyridinium)acetyl]hydrazine dichloride.

2-(3-Hydroxy-1-methyl-2-pyridinemethylene)-1-[2-(1-methyl-1-piperidinium)acetyl]hydrazine dichloride.

2-(5-Hydroxy-1-methyl-2-pyridinemethylene)-1-[2-(trimethylammonium)acetyl]hydrazine dichloride.

1-[2-(4-Chloro-1-pyridinium)acetyl]-2-(5-hydroxy-1-methyl-2-pyridinemethylene) hydrazine dichloride.

1-[2-(3-Carboxy-1-isoquinolinium)acetyl]-2-(5-hydroxy-1-methyl-2-pyridinemethylene) hydrazine dichloride.

1-[2-(2-Carboxy-4-methoxy-1-quinolinium)acetyl]-2-(5-hydroxy-1-methyl-2-pyridinemethylene) hydrazine dichloride.

2-(5-Hydroxy-1-methyl-2-pyridinemethylene)-1-[2-(3-hydroxy-1-pyridinium)acetyl]hydrazine dichloride.

2-(5-Hydroxy-1-methyl-2-pyridinemethylene)-1-[2-(1-methyl-1-piperidinium)acetyl]hydrazine dichloride.

2-(1-Methyl-2-pyridinemethylene)-1-[2-(1-pyridinium)acetyl]hydrazine dichloride (5b).

O-Benzyl-N-(1,6-dimethyl-3-hydroxy-2-pyridinemethylene) hydroxylamine chloride.

It has been found that the novel pyridinium compounds of this invention are good acetylcholinesterase inhibitors in vitro as shown in Tables I and II. The pyridinium compounds also have good activity in vivo as prophylactics and antidotes against nerve agent poisoning as shown in Tables III–VI.

Competitive Inhibition of Acetylcholinesterase. The reversible inhibition studies on electric eel and human erythrocyte AChE were performed at 25°±1° C. in pH 7.6, 0.1M phosphate buffer containing 4% ethanol using S-acetyl thiocholine as a substrate (Ellman, G. L., Courtney, D., Andres, V., and Featherstone, R. M., *Biochem. Pharmacol.* 1961, 7, 88). For analysis of AChE inhibitory potency, electric eel AChE was dissolved in buffer. Human erythrocyte AChE was dissolved in a 0.01M borate buffer (pH 10.2) containing 0.01% protease free bovine serum albumin. 5,5'-Dithiobis(2-nitrobenzoic acid) (DTNB) and S-acetylthiocholine were prepared in phosphate buffer. All inhibitor solutions were also dissolved in phosphate buffer; some required the addition of 95% ethanol. Increasing absorbance during substrate hydrolysis was monitored on a Varian DMS-90 spectrometer. Duplicate studies were performed on separate days using fresh solutions. No time dependent inhibition was observed over a period of at least one hour. Using three different substrate concentrations and four inhibitor concentrations, a Dixon plot (1/activity vs. inhibitor conc.) was made and the $K_I$ values determined. The $K_I$ value is the dissociation constant of the enzyme-inhibitor complex. Inhibitors with lower $K_I$ values are more potent. In the case of poor inhibitors an $IC_{50}$ was determined by plotting AChE activity vs inhibitor concentration. Only values between 10% and 90% inhibition were used. The exact procedure is as follows.

First, 20 $\mu$L of S-acetylthiocholine (0.075M) and 100 $\mu$L of DTNB (0.10M) were mixed together with phosphate buffer. Inhibitor was then added and the solution mixed well. Next, 50 $\mu$L of electric eel AChE (1.5 units/mL) was added and the solution mixed again. With human enzyme, 20 $\mu$L of a 2 units/mL stock solution was added. Increasing absorbance was monitored at 412 nm. Controls were used for each run in the case of inhibitors that absorb highly at 412 nm. Hydrolysis rates of all inhibitors were negligible. Total volume and organic solvent, if any, was kept constant.

Aldoximes (1a,b,d,e) showed pure competitive inhibition of AChE whereas the semicarbazones (3a,b, 4b) and acyl hydrazones (5a, 5b) showed mixed-type inhibition of AChE (linear, noncompetitive). Results are summarized in Table I.

The 3-hydroxy substituted aldoximes did not inhibit either enzyme well, but did show some selectively for the electric eel enzyme. The 3-hydroxy derivative of 2-PAM was also tested and did not inhibit either enzyme at concentrations up to 1 mM. Addition of a benzyl group to the aldoxime of 3-hydroxy-2-PAM (1b) improves binding and 1b has an $IC_{50}$ of 500 $\mu$M with electric eel AChE. The methylaldoxime 1c did not inhibit either enzyme at concentrations up to 1 mM. Without the 3-hydroxy substituent, tighter binding occurs and $K_I$ values of 40 $\mu$M and 100 $\mu$M were observed with eel and human enzymes respectively for the benzyl aldoxime 1a.

The bis-pyridinium acyl hydrazones 5a-b were the tightest binding reversible inhibitors with 5a having $K_I$ values of 10 and 20 $\mu$M with electric eel and human erythrocyte AChE, respectively. However, 3-hydroxy substitution did not have the same effect on acyl hydrazones as with the aldoximes. In this case a 3-hydroxy group improved the binding to AChE. The complex kinetics of 5b indicate at least two different binding modes for this inhibitor. At concentrations up to 75 $\mu$M, 5b acts as a noncompetitive inhibitor. However, at higher concentrations, 5b is an uncompetitive inhibitor. Only noncompetitive kinetics were observed for 5a.

All of the semicarbazones (3a,b, 4b) also exhibited noncompetitive kinetics. In addition, multiple binding was observed and compound 3b had two distinct $K_I$ values of 30 $\mu$M and 340 $\mu$M with electric eel AChE. Addition of a phenyl group to give the semicarbazone 3b resulted in a decrease of the $IC_{50}$ to 240 $\mu$M with the human enzyme. From the kinetic results, it appears that binding in a hydrophobic pocket near the active site is the most important interaction for the semicarbazones. Compound 4b is the most indicative of this trend. Unlike all other carbamates, it is not a time dependent inhibitor indicating that its position near the active site serine is not equivalent to that occupied by the aldoximes 2a-c in the E.I complex. Also, the 3-hydroxyl group does not negatively influence binding as with the 3-hydroxy aldoximes which further indicates that binding of the semicarbazones is different from the aldoximes.

Irreversible Inhibition of Acetylcholinesterase. The irreversible inhibition studies of electric eel and human erythrocyte AChE were performed at 25°±1° C. in 0.1M phosphate buffer. Inhibitor and enzyme were incubated in a buffer solution of 1.0 mL total volume and 100 $\mu$L aliquots were taken at 1 min intervals. The aliquots were added to freshly prepared assay solutions containing 20 $\mu$L of S-acetylthiocholine, 100 $\mu$L of DTNB, and 2280 $\mu$L of buffer. Increasing absorbance was monitored at 412 nm. Pseudo first order inhibition constants were determined by measuring the enzymatic activity of acetylcholinesterase after incubating the enzyme with inhibitor for various time periods. Second order inhibition rate constants $k_{obs}/[I]$ are reported in Table II. Inhibitors with higher $k_{obs}/[I]$ values are more potent. Half-lives for inactivation ranged from 10.8 min for 4a to about 9 sec for 2c. The $k_{obs}/[I]$ for 2c was estimated at $>110,000 M^{-1}s^{-1}$ because its rapid inactivation of AChE made it difficult to accurately determine its inhibitory potency. Compounds 2a-c are novel analogs of 2-PAM that also incorporate a dimethylcarbamyl substituent that reacts covalently with AChE. Compounds 2a and 2c have greater anti AChE activity in vitro with human AChE than either pyridostigmine or physostigmine. A notable selectivity for the human enzyme was observed for all of the carbamates. The semicarbazone 4a inactivated AChE very slowly. In contrast, the phenyl substituted semicarbazone carbamate 4b was not a time dependent inhibitor of AChE over a period of 1.5 hours, unlike all other carbamates tested. Both compounds have similar $K_I$ values with electric eel AChE; 4a has a $K_I$ of 100 μM and 4b has a $K_I$ of 85 μM. A $K_I$ for the human enzyme could not be determined for 4a because of its rapid inactivation of AChE at inhibitor concentrations exceeding 10 times the enzyme concentration.

Animal Studies-Pretreatment Activity. All animal studies were carried out at Battelle, Inc., in Columbus, OH. The results of in vivo mouse evaluations against GD for the compounds tested as intramuscular (i.m.) or oral pretreatment agents are given in Tables III and IV respectively and were obtained as follows. Male ICR mice from Charles River (20 to 30 g average weight) were treated with three different doses of the pyridinium test compound i.m. 15 or 60 min, or by gavage 30 or 120 min before challenge with a dose of $2 \times LD_{50}$ of GD ($LD_{50}=98$ μg/kg without atropine, $LD_{50}=130$ μg/kg with 11.2 mg/kg of atropine). The 24 h $LD_{50}$ of the test compounds administered i.m. or orally were determined using 5-7 dose groups with 5 animals per dose. As a negative reference treatment, saline was administered instead of the test compound. As a positive control for survival, pyridostigmine (0.1 mg/kg, i.m.; 0.82 mg/kg, orally) was administered to a separate group of animals. All pretreatment groups received atropine sulfate (11.2 mg/kg) and 2-PAM (25 mg/kg) i.m. exactly 10 seconds after GD challenge, using a total dose volume of 0.5 mL/kg body weight. All animals were allocated to pretreatment cells in a randomized block design. Groups of ten mice were used in each experiment and survivors in each group were noted after 24 h. The 24-hour survival of animals pretreated with each dose of the pyridinium test compound was compared with the 24-hour survival observed in the negative reference pretreatment group. A survival difference of at least four is required to identify improved efficacy of the candidate over that observed with the negative reference pretreatment.

Compounds 2a-d, 4a-b, 5a-b were excellent pretreatment agents, affording significant protection against a dose of $2 \times LD_{50}$ of GD. In all cases saline solution was used as the baseline standard (all mice die) and pyridostigmine as the positive control for survival (80-100% of the mice survive).

Carbamate derivatives 2a-2d showed 70 to 90% survival rates at selected doses. After 15 min pretreatment with compound 2a, 2b, or 2d 90% of mice survive a challenge of $2 \times LD_{50}$ of GD at comparable fractions of the $LD_{50}$'s for these compounds (1/55 $LD_{50}$ of 2a, 1/72 $LD_{50}$ of 2b, 1/67 $LD_{50}$ of 2d). On the other hand, compound 2c afforded a 70% survival rate under the same conditions but at a 1/16,700 fraction of its $LD_{50}$. Carbamate semicarbazones 4a and 4b and the acyl hydrazones 5a and 5b were also very good i.m. pretreatment agents. Carbamate semicarbazone 4a was exceptionally good as a pretreatment agent. Acyl hydrazones 5a and 5b were also excellent pretreatment agents but their effective doses were much closer to their toxic doses than was the case with 4a. Except for 4a, all remaining pretreatment agents were more effective when given 15min prior to Soman challenge. The decrease in efficacy at 60 min may be due to transformation of the drugs to inactive metabolites and/or clearance from the animal. It was most noticeable for acyl hydrazones 5a and 5b, which was doubly charged and can be excreted more rapidly. All seven pretreatment agents offered comparable or better protection against GD than the positive control, pyridostigmine.

Carbamate derivatives 2a-2c and carbamate semicarbazone 4b showed excellent activity in the oral pretreatment studies. They afforded 80-100% survival rates at 120 min prior to nerve agent challenge while pyridostigmine alone allowed no survival. In contrast to its good activity in the i.m. studies, bis-pyridinium acyl hydrazone 5a was not good as an oral pretreatment agent. This may be due to fast clearance from the animal requiring higher doses that approach the toxic dose.

Oximes 1a-1f and semicarbazones 3b, 3c and 3d were inactive in the i.m. pretreatment assay. In the case of substituted oxime derivatives a 3-hydroxy substituent significantly reduces drug toxicity (1a>1b). On the other hand increasing the steric bulk of the oxyimino substituent increases drug toxicity (1b>1c).

Animal Studies-Reactivator Activity. The results of in vivo mouse evaluations against GD and GA for the compounds tested as OP reactivators are given in Tables V and VI and were obtained as follows. Male ICR mice from Charles River (20 to 30 g average weight) were treated with the pyridinium test compound at three different doses administered i.m. 10 seconds after challenge with $2 \times LD_{50}$ of GD or GA (aqueous solution containing 0.9% NaCl). The test compound was always given simultaneously with atropine sulfate (11.2 mg/kg). As a negative reference treatment group, atropine sulfate (11.2 mg/kg) and 2-PAM (25 mg/kg) were given without the pyridinium test compound (no mice survive). As a positive control for survival, HI-6 (9.6 mg/kg) was administered with atropine sulfate (11.2 mg/kg) to a separate group of animals. All injections were administered i.m. using a dose volume of 0.5 mL/kg body weight. All animals were allocated to treatment cells in a randomized block design. Groups of ten mice were used in each experiment and survivors in each group were noted after 24 h. The 24-hour survival of animals injected with each dose of test compound was compared to the 24-hour survival observed in the negative reference treatment cell. A survival difference of at least four is required to identify improved efficacy of the candidate over that observed with the reference treatment. An alternate procedure used on some compounds was the adjunct efficacy test: the pyridinium test compound was always given simultaneously with atropine sulfate (11.2 mg/kg) and 2-PAM (25 mg/kg). The rest of the procedure is as described above.

Carbamate oxime derivatives 2a, 2b, semicarbazone 3a, carbamate semicarbazone 4b and bis-pyridinium acyl hydrazones 5a and 5b showed significant activity as GD reactivators (Table V). The last two also showed significant activity as GA reactivators (Table VI). 2-PAM was used as the baseline standard while the positive control used HI-6 as the reactivator. Carbamate oximes 2a and 2b afforded 50% and 70% survival rates respectively at a dose 1/16 of their $LD_{50}$'s. They were also the most toxic of the five derivatives that showed activity as OP reactivators. The greater inhibition of AChE displayed by 2a compared to 2b is matched by its greater toxicity. A 62 fold increase in $k_{obs}/[I]$ accompanied by a 44 fold increase in toxicity indicates that in the case of irreversible inhibitors a compromise must be reached between the degree of inhibition that affords protection from the OP agent and that which prevents the enzyme from performing its physiological role. It is noteworthy that 2a and 2b must be acting as prodrugs of the actual OP reactivator since they do not possess a nucleophile themselves that can displace the OP from the active site of AChE. In the semicarbazone series, a 3-hydroxy substituent increases in vivo activity (3a>>3c). Semicarbazone 3a afforded 70% survival rate at 1/25 of its $LD_{50}$ when given 10 seconds after a challenge of $2\times LD_{50}$ of Soman. Semicarbazone 3a was also an excellent reactivator when tested in the adjunct assay: it afforded 90% survival rate when administered along with 2-PAM (25 mg/kg) 10 seconds after Soman challenge. This combination of drugs was more effective than HI-6 in counteracting Soman intoxication. Carbamate semicarbazone 4b afforded 50% survival rate at 1/16 of its $LD_{50}$ when given 10 sec after a challenge of $2\times LD_{50}$ of Soman. Bis-pyridinium acyl hydrazone 5a was an excellent GD reactivator. It afforded 90% survival rate at a dose of 73 mmol/kg (approx. $\frac{1}{8}$ $LD_{50}$) when given 10 seconds after Soman challenge.

Two hydroxy 2-PAM derivatives (1f, 1g) were prepared and tested for comparison with 2-PAM and with the other substituted oxime derivatives reported in this study. The parent 2-PAM is not an effective reactivator against Soman due to rapid "aging" of the inhibited AChE. Adding a hydroxy substituent to the 3 or 5 position of 2-PAM resulted in no improvement in reactivating ability concurrent with a small increase in toxicity. In addition, these derivatives were not significantly better than 2-PAM in the pretreatment assay. The carbamate of 5-hydroxy-2-PAM chloride, compound 2d, incorporates the structural features of pyridostigmine and 2-PAM. It afforded 90% survival rate at a dose 1/67 of its $LD_{50}$ when given 15 or 60 minutes prior to Soman challenge.

Summary-Animal Studies. The in vivo activity described herein for some of the novel pyridinium compounds of this invention can be summarized as follows: eight compounds (2a-2d, 4a, 4b, 5a, 5b) were effective i.m. prophylactics against GD; four compounds (2a-2c, 4b) were effective oral prophylactics against GD; six compounds (2a, 2b, 3a, 4b, 5a, 5b) were good in vivo reactivators against GD; two compounds (5a, 5b) were good in vivo reactivators against GA; five compounds (2a, 2b, 4b, 5a, 5b) were both excellent prophylactics and good reactivators against GD. Compounds 4a and 3a form a set in which an excellent prophylactic (4a) is transformed by AChE into a good OP reactivator (3a). Structural requirements for prophylactic activity are a carbamate moiety and/or a second quaternary center. Since carbamates may act as prodrugs for the actual reactivators (i.e. 3a and 4a), the latter structural requirements also apply for AChE reactivators in addition to semicarbazones having a free OH group in the pyridine ring.

Drug Delivery. For the prophylaxis of OP poisoning and for the treatment of OP overdose, Myasthenia Gravis, senile dementia such as is seen in Alzheimer's and adult Down's syndrome patients, high blood pressure, glaucoma, and abdominal distension the pyridinium compounds of the present invention may be administered orally, topically or parenterally. The term parenteral as used includes subcutaneous injection, intravenous, intramuscular, intrasternal injection or infusion techniques. The dosage depends primarily on the specific formulation and on the object of the therapy or prophylaxis. The amount of the individual doses as well as the administration is best determined by individually assessing the particular case.

The pharmaceutical compositions containing the active ingredient may be in a form suitable for oral use, for example as tablets, troches, lozenges, aqueous or oily suspensions, dispersible powders or granules, emulsions, hard or soft capsules or syrups or elixirs. Dosage levels of the order to 0.2 mg to 140 mg per kilogram of body weight per day are useful in the treatment of above-indicated conditions (10 mg to 7 gms per patient per day). The amount of active ingredient that may be combined with carrier materials to produce a single dosage form will vary depending upon the host treated and the particular mode of administration.

For injection, the therapeutic amount of pyridinium compounds of the present invention will normally be in the dosage range from 0.2 mg to 140 mg/kg of body weight. Administration is made by intravenous, intramuscular or subcutaneous injection. Accordingly, pharmaceutical compositions for parenteral administration will contain in a single dosage form about 10 mg to 7 gms of pyridinium compound of the present invention. In addition to the active ingredient, these pharmaceutical compositions will usually contain a buffer, e.g. a phosphate buffer which keeps the pH in the range from 3.5 to 7 and also sodium chloride, mannitol or sorbitol for adjusting the isotonic pressure.

A composition for tonical application can be formulated as an aqueous solution, lotion, jelly or an oily solution or suspention. A composition in the form of an aqueous solution is obtained by dissolving the pyridinium compounds of the present invention in aqueous buffer solution of pH 4 to 8.5 and if desired, adding a polymeric binder. An oily formulation for topical application is obtained by suspending the pyridinium compounds of the present invention in an oil, optionally with the addition of a swelling agent such as aluminium stearate and/or a surfactant.

Synthetic Methods. All common chemicals and solvents were reagent grade or better. The purity of each compound was checked by $^1$H NMR, mass spectroscopy, thin-layer chromatography (TLC), and elemental analysis. Results are consistent with the proposed structures. Melting points were obtained on a Büchi capillary melting point apparatus and are uncorrected. $^1$H NMR spectra were recorded with a Varian Gemini 300 MHz NMR spectrometer; chemical shifts are reported in parts per million ($\delta$) from an internal tetramethylsilane standard. Mass spectra were recorded on a Varian Mat 112s spectrometer. Elemental analyses were performed by Atlantic Microlab in Atlanta, Ga. 3-Hydroxy-2-pyridine carboxaldehyde (Stempel, A. and Buzzi, E. C., *J. Am. Chem. Soc.* 1949, 71, 2969; Ginsburg, S. and Wilson, I. B., *J. Am. Chem. Soc.* 1957, 79, 481, incorporated herein by reference) was prepared from 3-hydroxy-2-hydroxymethyl pyridine by oxidation using manganese dioxide (Demerseman, P., Kiffer, D., Debussche, L., Lion, C., Royer, R., and S.-Roumanou, H., *Eur. J. Med. Chem.* 1988, 23, 63, incorporated herein by reference). Girard's reagent "P" [1-(carboxymethyl)pyridinium chloride], 4-phenylsemicarbazide, and 3-hydroxy-6-methyl-2-pyridinemethanol were purchased from Aldrich Chemical Company.

The oxime, hydrazone, semicarbazone and acyl hydrazone derivatives described herein were prepared using standard methodology. Many different O-substituted hydroxylamines can be prepared by known procedures (Grochowski, E. and Jurczak, J., *Synthesis* 1976, 682; Schumann, E. L., Heinzelman, R. V., Greig, M. E., and Veldkamp, W., *J. Med. Chem.* 1964, 7, 329, incorporated herein by reference) to afford the various substituted oximes described herein. Several substituted hydrazines are commercially available (i.e. methylhydrazine, 1,1-dimethylhydrazine, 1,1-diphenylhydrazine, from Aldrich Chemical Co.) and others can be synthesized by standard methodology (i.e. Hoffman degradation of ureas, reduction of N-nitroso compounds, reduction of diazonium salts) to afford the hydrazone derivatives described herein. Several substituted semicarbazides are commercially available (i.e. 4-phenyl-3-thiosemicarbazide, 4,4-diphenylsemicarbazide, 4,4-dimethyl-3-thiosemicarbazide, 4-ethyl-3-thiosemicarbazide) and others can be synthesized by standard methodology (reduction of N-nitro ureas). Commercially available Girard's reagent "T" [(carboxymethyl) trimethylammonium chloride hydrazide] can be used instead of Girard's reagent "P" to obtain 2-(trimethylammonium)acetyl hydrazine derivatives similar to 5a and 5b. Other hydrazides for the synthesis of various acyl hydrazones described herein can be made by known methodology (Vogel, A. I., in *A Textbook of Practical Organic Chemistry*; Longman Group Limited: London, 1972; pp. 976–978, incorporated herein by reference), which involves the reaction between an amine and ethyl chloroacetate, followed by reaction with hydrazine hydrate. Conversion of the 3 or 5-hydroxy moiety into a carbamate was accomplished using N,N-dimethylcarbamyl chloride. Other N,N-disubstituted carbamates can be made by reaction between commercially available triphosgene and a disubstituted amine, followed by reaction with the 3 or 5-hydroxy pyridine derivative. N-monosubstituted carbamates can be prepared by reaction of the free 3-OH group on the pyridine ring and any of numerous isocyanates that are commercially available. In the case of fluorinated derivatives, the synthesis of the appropiate fluoroalkylamine (some are commercially available) is required, followed by reaction with phosgene to generate the desired isocyanate. Quaternization of the pyridine nitrogen was carried out using methyl iodide in a sealed glass pressure vessel and was followed by anion exchange using a biphasic mixture of silver chloride and the methiodide in acetonitrile/water. Other salts of the pyridinium compounds described herein can be made in similar fashion, by methathesis involving the silver salt of the desired counterion and the methiodide formed in the initial alkylation of the pyridine nitrogen. The usefulness of this procedure has been studied with 2-PAM derivatives (Kondritzer, A. A., Ellin, R. I., and Edberg, L. J., *J. Pharm. Sci.* 1961, 50, 109, incorporated herein by reference).

The following examples are given to illustrate the invention and are not intended to limit it in any manner:

EXAMPLE 1

Preparation of
O-Benzyl-N-(1-methyl-2-pyridinemethylene)
Hydroxylamine Chloride (1a)

O-Benzyl-N-(2-pyridinemethylene) hydroxylamine. O-Benzylhydroxylamine hydrochloride (12.77 g, 0.08 mol) was added to a solution of NaOH (3.2 g, 0.08 mol) in 80 mL 1:1 EtOH/H$_2$O. Pyridine-2-carbaldehyde (7.6 mL, 0.08 mol) was added to this solution and the resulting mixture was stirred at room temperature for 10 h. Excess water was removed under vacuum and the residue was fractionally distilled under reduced pressure (14 mm Hg). The product was obtained as a yellow oil in the fraction distilling at 85°–90° C. (11.3 g, 67%). $^1$H NMR (Me$_2$SO-d$_6$) δ: 5.25 (s, 2H), 7.24 (t, 1H), 7.32–7.44 (m, 5H), 7.66 (t, 1H), 7.78 (d, 1H), 8.23 (s, 1H), 8.58 (d, 1H).

O-Benzyl-N-(1-methyl-2-pyridinemethylene)hydroxylamine iodide. Methyl iodide (14.3 mL, 0.23 mol) was added to a solution of O-Benzyl-N-(2-pyridinemethylene) hydroxylamine (11.3 g, 0.05 mol) in 75 mL of acetonitrile. The resulting mixture was heated in a pressure vessel at 65° C. for 24 h. The solvent was removed in vacuo and the residue was triturated with acetone to afford the product as a light orange solid (17.2 g, 92%), m.p. 125°–7° C. (dec.). $^1$H NMR (Me$_2$SO-d$_6$) δ: 4.36 (s, 3H), 5.38 (s, 2H), 7.36–7.49 (m, 5H), 8.09 (t, 1H), 8.36 (d, 1H), 8.55 (t, 1H), 8.84 (s, 1H), 9.00 (d, 1H).

O-Benzyl-N-(1-methyl-2-pyridinemethylene) hydroxylamine chloride. Silver chloride (freshly prepared from 14.6 g AgNO$_3$ and excess conc. HCl) was added to a solution of 16.2 g (0.05 mol) of O-Benzyl-N-(1-methyl-2-pyridinemethylene)hydroxylamine iodide in 800 mL H$_2$O. The suspension was vigorously stirred with a mechanical stirrer for 4 h at room temperature. The yellow precipitate was filtered off and the filtrate was concentrated to dryness and coevaporated several times with acetone. Traces of solvent are removed by evaporation at 50° C. in a rotary evaporator at 0.8 mm Hg overnight. The yellow solid that remains (11.63 g) is recrystallized from EtOH/acetone with scratching to obtain 8.1 g (68%) of analytically pure product as beige microscopic needles; m.p. 145°–6° C. (dec.). Anal. Calcd. for C$_{14}$H$_{15}$ClN$_2$O x H$_2$O: C, 61.87; H, 5.93; N, 10.31; Cl, 13.05. Found: C, 61.94; H, 5.94; N, 10.31; Cl, 13.10. $^1$H NMR (Me$_2$SO-d$_6$) δ: 4.38 (s, 3H), 5.38 (s, 2H), 7.36–7.48 (m, 5H), 8.09 (t, 1H), 8.35 (d, 1H), 8.86 (s, 1H), 9.08 (d, 1H).

O-(Diphenylmethyl)-N-(1-methyl-2-pyridinemethylene) hydroxylamine chloride O-(p-chlorobenzyl)-N-(1-methyl-2-pyridinemethylene) hydroxylamine chloride O-(p-methoxybenzyl)-N-(1-methyl-2-pyridinemethylene) hydroxylamine chloride O-(1-naphtylmethyl)-N-(1-methyl-2-pyridinemethylene) hydroxylamine chloride O-(2-methyl-1-naphtylmethyl)-N-(1-methyl-2-pyridinemethylene) hydroxylamine chloride, O-(2,3,4-trimethoxybenzyl)-N-(1-methyl-2-pyridinemethylene hydroxylamine chloride, and O-(3,3-diphenylpropyl)-N-(1-methyl-2-pyridinemethylene) hydroxylamine chloride can be made by the same procedure replacing O-benzyl hydroxylamine in the above example respectively with O-(diphenylmethyl) hydroxylamine, O-(p-chlorobenzyl) hydroxylamine, O-(p-methoxybenzy) hydroxylamine, O-(1-naphtylmethyl) hydroxylamine, O-(2-methyl-1-naphtylmethyl) hydroxylamine, O-(2,3,4-trimethoxybenzyl) hydroxylamine, and O-(3,3-diphenylpropyl) hydroxylamine.

EXAMPLE 2

Preparation of
O-Benzyl-N-(3-hydroxy-1-methyl-2-pyridinemethylene) hydroxylamine chloride (1b)

O-Benzyl-N-(3-hydroxy-2-pyridinemethylene) hydroxylamine. A solution of O-benzyl hydroxylamine was prepared by dissolving 2 g of sodium hydroxide (0.05 mol) and 8 g of O-benzyl hydroxylamine hydrochloride (0.05 mol) in 50 mL of 50% ethanol-water. To this solution was added 6.15 g of 2-formyl-3-hydroxypyridine (0.05 mol). The mixture was stirred for 3 h at room temperature. The precipitate was then filtered and air dried to yield 10.3 g (90.3%) of pure product; m.p. 64°–65° C. $^1$H NMR (CDCl$_3$) δ: 9.72 (s, 1H. OH); 8.37 (s, 1H, CH=N); 8.13 (d of d, J=2H, J=4Hz, 1H); 7.33 (m, 7H); 5.17 (s, 2H, CH$_2$). Anal. Calcd. for $C_{13}H_{12}N_2O_2$: C, 68.41; H, 5.30; N, 12.27. Found: C, 68.34; H, 5.32; N, 12.21.

O-Benzyl-N-(3-hydroxy-1-methyl-2-pyridinemethylene) hydroxylamine chloride. O-Benzyl-N-(3-hydroxy-2-pyridinemethylene) hydroxylamine (2.65 g, 11.6 mmol) was placed in a pressure tube together with 7 g of methyl iodide and 40 mL of a 2:3 mixture of EtOH/water. The reaction mixture was heated at 65° C. for 20 h and the solvent was then removed in vacuo. The residue was triturated with acetone to afford 2.50 g (58%) of product as greenish crystals; m.p. 247° C. (dec.). The methiodide salt (4.90 g, 13.2 mmol) was dissolved in 22 mL of a 1:1 mixture of acetonitrile and water and freshly made AgCl was then added (from 4.0 g $AgNO_3$ and excess conc. HCl, washed well with water). Additional water (15 mL) was added to this suspension and the resulting mixture was stirred at room temperature for 40 min. The silver iodide was removed by filtration and the filtrate was conmcentrated to dryness in vacuo to yield a residue that was triturated with acetone. The solid that resulted was washed well with acetone and dried to yield 3.61 g (98%) of product as white crystals; m.p. 146° C. $^1$H NMR (DMSO-$d_6$) δ: 8.58 (d, 1H, J=5.0 Hz), 8.55 (s, 1H), 8.20 (d, 1H, J=7.3 Hz), 7.90 (d of d, 1H), 7.42 (m, 5H), 5.34 (s, 2H), 4.27 (s, 3H). Anal. Calcd. for $C_{14}H_{15}N_2O_2Cl \times H_2O$: C, 56.65; H, 5.78; N, 9.43; Cl, 11.94. Found: C, 56.65; H, 5.79; N, 9.40; Cl, 11.88.

O-(1-Naphtylmethyl)N-(3-hydroxy-1-methyl-2-pyridinemethylene) hydroxylamine chloride, O-(2-methyl-1-naphtylmethyl)-N-(3-hydroxy-1-methyl-2-pyridinemethylene) hydroxylamine chloride, O-(2,3,4-trimethoxybenzyl)-N-(3-hydroxy-1-methyl-2-pyridinemethylene) hydroxylamine chloride, and O-(3,3-diphenylpropyl)-N-(3-hydroxy-1-methyl-2-pyridinemethylene) hydroxylamine chloride can be made by the same procedure replacing O-benzyl hydroxylamine in the above example respectively with O-(1-naphtylmethyl) hydroxylamine, O-(2-methyl-1-naphtylmethyl) hydroxylamine, O-(2,3,4-trimethoxybenzyl) hydroxylamine, and O-(3,3-diphenylpropyl) hydroxylamine. O-(1-Naphtylmethyl)-N-(5-hydroxy-1-methyl-2-pyridinemethylene) hydroxylamine chloride, O-(2-methyl-1-naphtylmethyl)-N-(5-hydroxy-1-methyl-2-pyridinemethylene) hydroxylamine chloride, O-(2,3,4-trimethoxybenzyl)-N-(5-hydroxy-1-methyl-2-pyridinemethylene) hydroxylamine chloride, and O-(3,3-diphenylpropyl)-N-(5-hydroxy-1-methyl-2-pyridinemethylene) hydroxylamine chloride can be made by the same procedure substituting 3-hydroxy-2-pyridine carbaldehyde for 2-formyl-5-hydroxy pyridine.

EXAMPLE 3

Preparation of
O-Methyl-N-(3-hydroxy-1-methyl-2-pyridinemethylene) hydroxylamine chloride (1c)

O-Methyl-N-(3-hydroxy-2-pyridinemethylene) hydroxylamine. NaOH (1.62 g, 0.04 mol) was added to a solution of methoxyamine hydrochloride (3.4 g, 0.04 mol) in 30 ml of $H_2O$. 3-Hydroxy-2-pyridine carboxaldehyde (5.0 g, 0.04 mol) was added to the clear solution, followed by 15 mL of EtOH. The reaction mixture was stirred at room temperature for 15 h and concentrated in vacuo to a minimum volume (approx. 5 mL). Water (15 mL) was added to this residue and the resulting solution was extracted with EtOAc (4×20 mL). The organic extract was dried ($MgSO_4$), filtered and concentrated in high vacuum to a yellow oil that crystallizes upons cooling in a bath of isopropanol-dry ice to yield 4.83 g (79%) of product as a white solid; m.p. 186°-7° C. (dec). $^1$H NMR (CDCl$_3$) δ: 9.82 (s, 1H); 8.35 (s, 1H); 8.21 (d of d, 1H, J=1.5 Hz, J=4.5 Hz); 7.30 (d of d, 1H, J=1.5 Hz, J=8.5 Hz); 7.19 (d of d, 1H, J=4.5 Hz, J=8.5 Hz).

O-Methyl-N-(3-hydroxy-1-methyl-2-pyridinemethylene) hydroxylamine iodide. Methyl iodide (8.9 mL, 0.14 mol) was added to a solution of O-methyl-N-(3-hydroxy-2-pyridinemethylene) hydroxylamine (4.83 g, 32 mmol) in 20 mL of acetonitrile. The reaction mixture was heated in a pressure glass bottle at 70° C. for 20 h and then concentrated to dryness in vacuo. The resulting yellow solid was triturated with acetone and filtered to yield 7.72 g (82%) of product which was used in the next step without further purification.

O-Methyl-N-(3-hydroxy-1-methyl-2-pyridinemethylene) hydroxylamine chloride. The methiodide obtained in the previous step (7.72 g, 26 mmol) was dissolved in 230 mL of $H_2O$. Freshly made AgCl (7.6 g, 53 mmol) was added to this solution and the resulting suspension was stirred at room temperature for 1.5 h. The reaction mixture was filtered and the filtrate was concentrated to dryness in vacuo. The white solid that resulted was triturated with warm (40° C.) acetone and filtered to yield 4.35 g (83%) of product; m.p. 186°-7° C. (dec.). $^1$H NMR (DMSO-$d_6$) δ: 8.62 (d, 1H, J=6.0 Hz); 8.48 (s, 1H); 8.31 (d, 1H, J=8.5 Hz); 7.93 (d of d, 1H, J=6.0 Hz, J=8.5 Hz). Anal. Calcd. for $C_8H_{11}N_2ClO_2$: C, 47.41; H, 5.47; N, 13.83; Cl, 17.50. Found: C, 47.47; H, 5.49; N, 13.76; Cl, 17.43.

O-Methyl-N-(5-hydroxy-1-methyl-2-pyridinemethylene) hydroxylamine chloride can be made by the same procedure replacing 3-hydroxy-2-pyridine aldehyde in the above example with 2-formyl-5-hydroxy pyridine. O-[2-(1-Methyl-1-piperidinium]ethyl]-N-(3-hydroxy-1-methyl-2-pyridinemethylene) hydroxylamine dichloride and O-[2-(trimethyl ammonium)ethyl]-N-(3-hydroxy-1-methyl-2-pyridinemethylene) hydroxylamine dichloride can be made by the same procedure replacing methoxyamine in the above example with O-[2-(1-piperidine)ethyl]hydroxylamine and O-[2-(dimethylamino)ethyl]hydroxylamine.

EXAMPLE 4

Preparation
O-(p-Chlorobenzyl)-N-(3-hydroxy-1-methyl-2-pyridinemethylene) hydroxylamine chloride (1d)

O-(p-Chlorobenzyl)hydroxylamine hydrochloride. The hydroxylamine hydrochloride was prepared by hydrazinolysis of the corresponding benzyloxyphthalimide. The phthalimide (15 g, 0.051 mol) was dissolved in DMF (75 mL) and MeOH (260 mL) and warmed to 60° C. The solution was treated with hydrazine monohydrate (5.7 g, 0.11 mol) and allowed to cool to room temperature for 3 h. The mixture was acidified to pH 2 with 2N HCl and filtered. The filtrate was evaporated to dryness and treated with 2N NaOH (75 mL). The oily product was extracted with ether, and the combined ether extracts were washed with $H_2O$, dried over anhydrous $K_2CO_3$, and concentrated in vacuo. The resulting oil was treated with ethereal hydrogen chloride to precipitate the product as a white solid. Recrystallization from EtOH gave the pure hydroxylamine hydrochloride as shiny white plates (9.5 g, 96%), m.p. 235° C. [lit. m.p. 245° C.; Schumann, E. L., Heinzelman, R. V., Greig, M. E., and Veldkamp, W., *J. Med Chem.* 1964, 7, 329]. $^1$H NMR (CDCl$_3$) d: 7.23(s, 4H); 5.00(s, 2H).

O-(p-Cyanobenzyl)hydroxylamine hydrochloride, O-(2-Hydroxy-4-nitrobenzyl) hydroxylamine hydrochloride, and O-(p-Carboxy benzyl)hydroxylamine hydrochloride can be made by the same procedure replacing p-chlorobenzyloxyphtalimide respectively with p-cyanobenzyloxyphtalimide, 2-hydroxy-4-nitrobenzyloxyphtalimide, and p-carboxybenzyl oxyphtalimide.

O-(p-Chlorobenzyl)-N-(3-hydroxy-2-pyridinemethylene) hydroxylamine. O-(4-Chlorobenzyl) hydroxylamine hydrochloride (9.75 g, 50 mmol) was neutralized with NaOH (2.0 g, 50 mmol dissolved in 20 mL H$_2$O). Ethanol (20 mL) was added to solubilize the resulting hydroxylamine. 3-Hydroxy-2-pyridinealdehyde (6.2 g, 50 mmol) dissolved in H$_2$O (150 mL) was added and the mixture heated on a steam bath for 30 min. The solution was cooled to room temperature. The product crystallized out as long pale yellow needles. The mixture was filtered to isolate the pure product (12.5 g, 96%), m.p. 89°-90° C. $^1$H NMR(CDCl$_3$) δ: 9.67 (s, 1H); 8.33 (s, 1H); 7.33-7.13 (m, 7H); 5.17 (s, 2H). Anal. Calcd. for C$_{13}$H$_{11}$N$_2$O$_2$Cl: C, 59.43; H, 4.23; N, 10.67; Cl, 13.49. Found: C, 59.43; H, 4.26; N, 10.64; Cl, 13.56.

O-(p-Chlorobenzyl)-N-(3-hydroxy-1-methyl-2-pyridinemethylene) hydroxylamine iodide. A solution of O-(p-chlorobenzyl)-N-(3-hydroxy-2-pyridinemethylene) hydroxylamine (1.0 g, 3.8 mmol) in EtOH (45 mL) was placed in a glass pressure tube. Methyl iodide (1 mL, 16.0 mmol) was then added, and the tube was sealed tightly. The tube was heated at 69° C. in an oil bath for 20 h. The solution was concentrated in vacuo. The oily residue was triturated with acetone to give the crude product as a yellow solid (1.46 g, 95%). Recrystallization from acetone gave the pure product as a shiny yellow solid (0.8 g, 52%), m.p. 164°-166° C. $^1$H NMR (CDCl$_3$/DMSO-d$_6$) δ: 8.83-8.67 (m, 2H); 8.13-7.67 (m, 2H); 7.33 (s, 4H); 5.00 (s, 2H); 4.43 (s, 3H). Anal. Calcd. for C$_{14}$H$_{14}$N$_2$O$_2$ClI: C, 41.55; H, 3.49; N, 6.92; Cl, 8.76; I, 31.36. Found: C, 41.62; H, 3.53; N, 6.92; Cl, 8.71; I, 31.28.

O-(p-Chlorobenzyl)-N-(3-hydroxy-1-methyl-2-pyridinemethylene) hydroxylamine chloride. To a solution of the corresponding pyridinium iodide (1.0 g, 2.47 mmol) in CH$_3$CN/H$_2$O (1:1, 15 mL) was added freshly made AgCl (from 0.54 g AgNO$_3$ and conc. HCl). The mixture was allowed to stir at room temperature for 1.5 h. It was then filtered through a bed of Celite. The solvent was removed in vacuo. Trituration of the residue with acetone gave the pure pyridinium chloride (0.72 g) in 93% yield, m.p. 175° C. (dec). $^1$H NMR (CDCl$_3$/DMSO-d$_6$) δ: 8.67 (m, 1H); 8.37 (m, 1H); 8.00-7.67 (m, 1H); 7.37 (s, 4H); 5.3 (s, 2H); 4.33 (s, 3H). Anal. Calcd. for C$_{14}$H$_{14}$N$_2$O$_2$Cl$_2$: C, 53.68; H, 4.51; N, 8.95; Cl, 22.64. Found: C, 53.76; H, 4.56; N, 8.92; Cl, 22.57.

O-(p-Cyanobenzyl)-N-(3-hydroxy-1-methyl-2-pyridinemethylene) hydroxylamine chloride, O-(2-hydroxy-4-nitrobenzyl)-N-(3-hydroxy-1-methyl-2-pyridinemethylene) hydroxylamine chloride, and O-(p-carboxybenzyl)-N-(3-hydroxy-1-methyl-2-pyridinemethylene) hydroxylamine chloride can be made by the same procedure replacing O-(p-chlorobenzyl) hydroxylamine respectively with O-(p-cyanobenzyl)-N-(3-hydroxy-2-pyridinemethylene) hydroxylamine, O-(2-hydroxy-4-nitrobenzyl)-N-(3-hydroxy-2-pyridinemethylene) hydroxylamine, and O-(p-carboxybenzyl)-N-(3-hydroxy-2-pyridinemethylene) hydroxylamine. O-(p-Chlorobenzyl)-N-(5-hydroxy-1-methyl-2-pyridinemethylene) hydroxylamine chloride, O-(p-cyanobenzyl)-N-(5-hydroxy-1-methyl-2-pyridinemethylene) hydroxylamine chloride, O-(2-hydroxy-4-nitro benzyl)-N-(5-hydroxy-1-methyl-2-pyridinemethylene) hydroxylamine chloride, and O-(p-carboxy benzyl)-N-(5-hydroxy-1-methyl-2-pyridinemethylene) hydroxylamine chloride can be made by the same procedure replacing 3-hydroxy-2-pyridine aldehyde with 2-formyl-5-hydroxy pyridine.

EXAMPLE 5

Preparation of O-(p-Methoxybenzyl)-N-(3-hydroxy-1-methyl-2-pyridinemethylene) hydroxylamine chloride (1e)

O-(p-Methoxybenzyl)-N-(3-hydroxy-2-pyridinemethylene) hydroxylamine. O-(p-methoxybenzyl) hydroxylamine (5.55 g, 29 mmol; Grochowski et al, 1976 and Schumann et al, 1964, vide supra) was added to a solution of NaOH (1.2 g, 29 mmol) in 15 mL H$_2$O. 3-Hydroxy-2-pyridine carbaldehyde (3.6 g, 29 mmol) was then added, followed by 15 mL of 95% EtOH and 10 mL of acetone. The reaction mixture was stirred at room temperature for 4 h and was then poured over 400 mL of crushed ice. A beige solid comes out of solution upon scratching the sides of the beaker. It was filtered, washed with water and dried to yield 7.03 g (93%) of product; m.p. 79°-81° C. $^1$H NMR (CDCl$_3$) δ: 9.85 (s, 1H); 8.38 (s, 1H); 8.19 (d of d, 1H); 7.36 (d of d, 2H); 7.28 (d of d, 1H); 7.18 (d of d, 1H); 6.93 (d of d, 2H); 5.15 (s, 2H); 3.82 (s, 3H).

O-(p-Methoxybenzyl)-N-(3-hydroxy-1-methyl-2-pyridinemethylene) hydroxylamine chloride. Methyl iodide (7.2 mL, 0.12 mol) was added to a solution of O-(p-methoxy)benzyl-N-(3-hydroxy-2-pyridinemethylene) hydroxylamine (3.72 g, 14 mmol) in 60 mL of acetonitrile. The resulting mixture was divided into three pressure glass vessels and heated at 70° C. for 3 days. The solvent was removed in vacuo and the residue was triturated with ether/acetone (3:1); after drying, the methiodide weighed 4.88 g (85%). It was dissolved in 500 mL H$_2$O and 300 mL of acetonitrile and freshly made AgCl (2 eq.) was then added. The suspension was stirred at room temperature for 1.5 h and then filtered through Celite. The filtrate was concentrated to dryness in vacuo and the residue was triturated with acetone/ether (1:1). The yellow solid was filtered, washed first with acetone/ether (1:1), then with ether and dried to yield 3.57 g (97%) of pure product, m.p. 183°-184° C. (dec.). $^1$H NMR (d$_6$DMSO) δ: 8.57 (d, 1H, J=6.1 Hz); 8.50 (s, 1H); 8.19 (d, 1H, J=8.2 Hz); 7.88 (d of d, 1H, J=6.1 Hz, J=8.2 Hz); 7.38 (d, 2H, J=8.7 Hz); 6.95 (d, 2H, J=8.7 Hz); 5.25 (s, 2H); 4.26 (s, 3H); 3.75 (s, 3H). Anal. Calcd. for C$_{15}$H$_{17}$ClN$_2$O$_3$ x 0.55H$_2$O: C, 6.53; H, 5.73; N, 8.79; Cl, 11.13. Found: C, 56.53; H, 5.72; N, 8.79; Cl, 11.18.

O-(p-Dimethylaminocarbonyloxybenzyl)-N-(3-hydroxy-1-methyl-2-pyridinemethylene) hydroxylamine chloride, O-(p-propylaminocarbonylbenzyl)-N-(3-hydroxy-1-methyl-2-pyridinemethylene) hydroxylamine chloride, and O-(p-ethoxycarbonyl benzyl)-N-(3-hydroxy-1-methyl-2-pyridinemethylene) hydroxylamine chloride can be made by the same procedure replacing O-(p-methoxybenzyl) hydroxylamine in the above example respectively with O-(p-dimethylaminocarbonyloxy benzyl) hydroxylamine, O-(p- propylaminocarbonyl benzyl) hydroxylamine, and O-(p-ethoxycarbonyl benzyl) hydroxylamine. O-(p-Methoxybenzyl)-N-(5-hydroxy-1-methyl-2-pyridinemethylene) hydroxylamine chloride, O-(p-dimethylaminocarbonyloxy benzyl)-N-(5-hydroxy-1-methyl-2-pyridinemethylene) hydroxylamine chloride, O-(p-propylaminocarbonyl benzyl)-N-(5-hydroxy-1-methyl-2-pyridinemethylene) hydroxylamine chloride, and O-(p-ethoxycarbonyl benzyl)-N-(5-hydroxy-1-methyl-2-pyridinemethylene) hydroxylamine chloride can be made by the same procedure replacing 3-hydroxy-2-pyridine aldehyde in the above example with 2-formyl-5-hydroxy pyridine.

EXAMPLE 6

Preparation of
O-Benzyl-N-[3-(N',N'-dimethylcarbamoyl)hydroxy-1-methyl-2-pyridinemethylene]hydroxylamine chloride (2a)

O-Benzyl-N-[3-(N',N'-dimethylcarbamoyl)hydroxy-2-pyridinemethylene]hydroxylamine. Dimethylcarbamyl chloride (7 mL, 76 mmol) was added to a solution of 2.59 g (11 mmol) of O-benzyl-N-(3-hydroxy-2-pyridinemethylene]hydroxylamine (prepared as reported on previous page) in 20 mL of pyridine. The resulting mixture was stirred at 65° C. for 12 h and poured over 400 mL of ice water. The aqueous solution was extracted with ether (6×50 mL); the ether layer was dried ($Na_2SO_4$), filtered and concentrated to dryness to a yellow oil which was coevaporated with $H_2O$ and with acetone to remove the remaining pyridine. The residue was dissolved in 10 mL acetone, and water was added with cooling and stirring until no more precipitate came out of solution. The white solid was filtered, washed with water and dried to yield 3.02 g (89%) of product; m.p. 65°–66° C. $^1H$ NMR ($CDCl_3$) δ: 8.54 (d of d, 1H, J=4Hz, J=1Hz); 8.38 (s, 1H); 7.54 (d of d, 1H, J=8.3 Hz, J=1.5 Hz); 7.30–7.43 (m, 6H); 5.30 (s, 2H); 3.06 (s, 3H); 2.97 (s, 3H).

O-Benzyl-N-[3-(N',N'-dimethylcarbamoyl)hydroxy-1-methyl-2-pyridinemethylene]hydroxylamine iodide. A solution of 2.95 g (9.9 mmol) of O-benzyl-N-[3-(N',N'-dimethylcarbamoyl)hydroxy-2-pyridinemethylene] hydroxylamine and 2.8 mL (44 mmol) of methyl iodide in 20 mL of acetonitrile was heated at 65° C. in a glass pressure bottle for 2 days. The reaction mixture was concentrated to dryness to a dark orange oil which was triturated with cold acetone to yield a bright yellow precipitate that was washed with acetone and ether. After drying the product weighed 4.02 g (92%).

O-Benzyl-N-[3-(N',N'-dimethylcarbamoyl)hydroxy-1-methyl-2-pyridinemethylene]hydroxylamine chloride. The methiodide obtained in the previous step (4.02 g, 9 mmol) was dissolved in 25 mL $H_2O$ and 20 mL acetonitrile. Freshly prepared AgCl (2.61 g, 18 mmol) was added to this solution and the resulting suspension was stirred at room temperature for 1 h. The reaction mixture was filtered and the filtrate was concentrated to dryness to a white solid that was triturated with warm (40° C.) acetone for 20 min and filtered. The white solid was washed with acetone and ether to yield 3.2 g (quantitative) of the pure chloride, m.p. 150°–152° C. (dec.); $^1H$ NMR (DMSO-$d_6$) δ: 9.09 (d, J=5.5 Hz, 1H); 8.74 (s, 1H); 8.59 (d, J=8.4 Hz, 1H); 8.19 (d of d, J=8.4 Hz, J=5.5 Hz, 1H); 7.42 (m, 5H); 5.33 (s, 2H); 4.39 (s, 3H); 2.98 (s, 3H); 2.92 (s, 3H). Anal. Calcd. for $C_{17}H_{20}ClN_3O_3$ x 0.45 $H_2O$: C, 57.04; H, 5.89; N, 11.74; Cl, 9.91. Found: C, 56.99; H, 5.95; N, 11.69; Cl, 9.91.

O-Benzyl-N-[3-(N',N'-diethylcarbamoyl)hydroxy-1-methyl-2-pyridinemethylene]hydroxylamine chloride and O-benzyl-N-[3-(N',N'-difluoroethylcarbamoyl)hydroxy-1-methyl-2-pyridinemethylene]hydroxylamine chloride can be made by the same procedure replacing N,N-dimethylcarbamoyl chloride respectively with N,N-diethylcarbamoyl chloride and N,N-difluoroethylcarbamoyl chloride. O-Benzyl-N-[5-(N',N'-dimethylcarbamoyl) hydroxy-1-methyl-2-pyridinemethylene]hydroxylamine chloride, O-benzyl-N-[5-(N',N'-diethylcarbamoyl)hydroxy-1-methyl-2-pyridinemethylene]hydroxylamine chloride and O-benzyl-N-[5-(N',N'-difluoroethylcarbamoyl)hydroxy-1-methyl-2-pyridinemethylene]hydroxylamine chloride can be made by the same procedure replacing 3-hydroxy-2-pyridine aldehyde with 2-formyl-5-hydroxy pyridine. O-[2-(1-Methyl-1-piperidinium)ethyl]-N-[3-(N',N'-dimethylcarbamoyl)hydroxy-1-methyl-2-pyridinemethylene]hydroxylamine dichloride, and O-[2-(trimethylammonium)ethyl]-N-[3-(N',N'-dimethylcarbamoyl)hydroxy-1-methyl-2-pyridinemethylene]hydroxylamine dichloride can be made by the same procedure replacing O-benzylhydroxylamine in the above example with O-[2-(1-piperidine)ethyl]hydroxylamine and O-[2-(dimethylamino)ethyl]hydroxylamine.

EXAMPLE 7

Preparation of
O-(Diphenylmethyl)-N-[3-(N',N'-dimethylcarbamoyl)-hydroxy-1-methyl-2-pyridinemethylene]hydroxylamine chloride (2b)

O-(Diphenylmethyl)-N-(3-hydroxy-2-pyridinemethylene]hydroxylamine. O-Diphenylmethyl hydroxylamine (3.4 g, 14.4 mmol; Grochowski et al, 1976 and Schumann et al, 1964, vide supra) was added to a solution of NaOH (0.58 g, 14.4 mmol) in 7 mL of water. 3-Hydroxy-2-pyridine carbaldehyde (1.8 g, 14.4 mmol) was added to this solution and the resulting mixture was stirred at room temperature for 4 h. The white solid in the reaction mixture was filtered, washed with $H_2O$/EtOH (1:1) and dried to yield 3.17 (72%) of product, m.p. 82°–83° C. $^1H$ NMR ($CDCl_3$) δ: 9.60 (s, 1H); 8.51 (s, 1H); 8.2 (d of d, 1H); 7.30–7.43 (m, 10H); 7.23 (d of d, 1H); 7.16 (d of d, 1H); 6.29 (s, 1H).

O-(Diphenylmethyl)-N-[3-(N',N'-dimethylcarbamoyl)hydroxy-2-pyridinemethylene]hydroxylamine. Dimethylcarbamyl chloride (9 mL, 98 mmol) was added to a solution of O-(diphenylmethyl)-N-(3-hydroxy-2-pyridinemethylene]hydroxylamine (3.0 g, 9.9 mmol) in 30 mL of pyridine. The resulting mixture was stirred at room temperature for 14 h and poured over 400 mL of crushed ice. A white solid precipitates upon scratching the sides of the beaker. It was filtered, washed thoroughly with water and dried to yield 3.47 g (94%) of product, m.p. 89°–90° C. $^1H$ NMR ($d_6$-DMSO) δ: 8.49 (d of d, 1H); 8.37 (s, 1H); 7.64 (d of d, 1H); 7.47 (d of d, 1H); 7.42–7.28 (m, 10H); 6.29 (s, 1H); 2.81 (s, 3H); 2.74 (s, 3H).

O-(Diphenylmethyl)-N-[3-(N',N'-dimethylcarbamoyl)hydroxy-1-methyl-2-pyridinemethylene]hydroxylamine chloride. Methyl iodide (2.8 mL, 46 mmol) was added to a solution of O-(diphenylmethyl)-N-[3-(N',N'-dimethylcarbamoyl)hydroxy-2-pyridinemethylene] hydroxylamine (3.44 g, 9.2 mmol) in 40 mL of acetonitrile. The resulting mixture was divided into two pressure glass vessels and heated at 70° C. for 3 days. The solvent was removed in vacuo and the residue (4.92 g) was dissolved in a mixture of acetonitrile/water (200 mL:200 mL). Freshly made AgCl (2 eq, washed well with $H_2O$) was added to this solution and the resulting suspension was stirred at room temperature for 2 h. It was filtered through Celite and the filtrate was concentrated to dryness in vacuo to a residue that was triturated with ether. The white solid was collected by filtration and dried to yield 3.84 g (98%) of pure product, m.p. 153°–154° C. (dec.). $^1$H NMR ($d_6$-DMSO) δ: 9.06 (d, 1H, J=6.0 Hz); 8.87 (s, 1H); 8.55 (d, 1H, J=8.4 Hz); 8.18 (d of d, 1H, J=6.0 Hz, J=8.4 Hz); 7.45–7.30 (m, 10H); 6.44 (s, 1H); 4.35 (s, 3H); 2.8 (s, 3H); 2.79 (s, 3H). Anal. Calcd. for $C_{23}H_{24}ClN_3O_3$ x 1.19 $H_2O$: C, 61.76; H, 5.94; N, 9.39; Cl, 7.93. Found: C, 61.76; H, 6.02; N, 9.41; Cl, 7.97.

O-(Diphenylmethyl)-N-[3-(N'-isopropylcarbamoyl)-hydroxy-1-methyl-2-pyridinemethylene]hydroxylamine chloride and O-(diphenylmethyl)-N-[3-[N'-(2-fluoroethyl)carbamoyl]hydroxy-1-methyl-2-pyridinemethylene]hydroxylamine chloride can be made by the same procedure replacing N,N-dimethylcarbamyl chloride respectively with isopropyl isocyanate and 2-fluoroethyl isocyanate. O-(Diphenylmethyl)-N-[5-(N'-isopropylcarbamoyl)hydroxy-1-methyl-2-pyridinemethylene]hydroxylamine chloride and O-(diphenylmethyl)-N-[5-[N'-(2-fluoroethyl)carbamoyl]hydroxy-1-methyl-2-pyridinemethylene]hydroxylamine chloride can be made by the same procedure replacing 3-hydroxy-2-pyridine aldehyde with 2-formyl-5-hydroxy pyridine.

EXAMPLE 8

Preparation of O-(p-Methoxybenzyl)-N-[3-(N',N'-dimethylcarbamoyl)hydroxy-1-methyl-2-pyridinemethylene]hydroxylamine chloride (2c)

O-(p-Methoxybenzyl)-N-[3-(N',N'-dimethylcarbamoyl)hydroxy-2-pyridine methylene]hydroxylamine. Dimethylcarbamyl chloride (10 mL, 0.11 mol) was added to a solution of O-(p-methoxybenzyl)-N-(3-hydroxy-2-pyridinemethylene) hydroxylamine (3.3 g, 12.8 mmol) in 30 mL of pyridine. The resulting mixture was stirred at room temperature for 14 h and then poured over 400 mL of crushed ice. Since it was not possible to induce precipitation of the product, the aqueous mixture was extracted with ether (4×100 mL) and the organic extract was concentrated to dryness in vacuo. The oily residue was coevaporated with water to remove traces of pyridine and then with acetone. The 300 MHz $^1$H NMR of the resulting yellow oil shows no pyridine or water and was used in the next step without further purification.

O-(p-Methoxybenzyl)-N-[3-(N',N'-dimethylcarbamoyl)hydroxy-1-methyl-2-pyridinemethylene]hydroxylamine chloride. Methyl iodide (2.9 mL, 46.4 mmol) was added to each of two pressure glass tubes containing a solution of O-(p-methoxybenzyl)-N-[3-(N',N'-dimethylcarbamoyl)hydroxy-2-pyridinemethylene]hydroxylamine (3.82 g, 11.6 mmol, divided into two) in 40 mL of acetonitrile. The sealed reaction vessels were heated at 70° C. for 3 days and then the solvent was removed in vacuo. The resulting oil crystallizes upon standing at 0°–5° C. for 14 h in a 2:1 mixture of acetone/ether (75 mL). The yellow solid was filtered, washed with ether and dried to yield 4.94 g (90%) of crude methiodide. It was dissolved in 1:1 mixture of $H_2O$/acetonitrile (200 mL) and then freshly made AgCl (21 mmol, washed well with water) was added. The resulting suspension was stirred at room temperature for 2 h and filtered through Celite. The filtrate was concentrated to dryness in vacuo and the residue was triturated with 1:1 acetone/ether. The white solid that resulted was filtered, washed with ether and dried to yield 3.72 g (84.4%) of pure chloride, m.p. 145°–6° C. (dec.). Anal. Calcd. for $C_{18}H_{22}ClN_3O_4 \times 0.5$ $H_2O$: C, 55.59; H, 5.96; N, 10.81; Cl, 9.12. Found: C, 55.59; H, 6.03; N, 10.76; Cl, 9.17.

O-(p-Methoxybenzyl)-N-[3-(N',N'-dimethylcarbamoyl)hydroxy-1-ethyl-2-pyridinemethylene]hydroxylamine chloride, O-(p-methoxybenzyl)-N-[3-(N',N'-dimethylcarbamoyl)hydroxy-1-benzyl-2-pyridinemethylene]hydroxylamine bromide, O-(p-methoxybenzyl)-N-[3-(N',N'-dimethylcarbamoyl)hydroxy-1-(1-naphtylmethyl)-2-pyridinemethylene]hydroxylamine chloride, O-(p-methoxybenzyl)-N-[3-(N',N'-dimethylcarbamoyl)hydroxy-1-(2-methyl-1-naphtylmethyl)-2-pyridinemethylene]hydroxylamine chloride, O-(p-methoxybenzyl)-N-[3-(N',N'-dimethylcarbamoyl)hydroxy-1-diphenylmethyl-2-pyridinemethylene]hydroxylamine chloride, O-(p-methoxybenzyl)-N-[3-(N',N'-dimethylcarbamoyl)hydroxy-1-(2-hydroxy-4-nitrobenzyl)-2-pyridinemethylene]hydroxylamine chloride, O-(p-methoxybenzyl)-N-[3-(N',N'-dimethylcarbamoyl)hydroxy-1-(p-carboxybenzyl)-2-pyridinemethylene]hydroxylamine chloride, and O-(p-methoxybenzyl)-N-[3-(N',N'-dimethylcarbamoyl)hydroxy-1-(p-cyanobenzyl)-2-pyridinemethylene]hydroxylamine chloride can be made by the same procedure replacing methyl iodide in the above example respectively with ethyl iodide, benzyl bromide, 1-chloromethyl naphtalene, 1-chloromethyl-2-methyl naphtalene, chlorodiphenylmethane, 2-chloromethyl-4-nitrophenol, 4-chloromethyl benzoic acid, and 4-cyano benzyl chloride. O-(p-Methoxybenzyl)-N-[5-(N',N'-dimethylcarbamoyl)hydroxy-1-methyl-2-pyridinemethylene]hydroxylamine chloride, O-(p-methoxybenzyl)-N-[5-(N',N'-dimethylcarbamoyl)hydroxy-1-ethyl-2-pyridinemethylene]hydroxylamine chloride, O-(p-methoxybenzyl)-N-[5-(N',N'-dimethylcarbamoyl)hydroxy-1-benzyl-2-pyridinemethylene]hydroxylamine bromide, O-(p-methoxybenzyl)-N-[5-(N',N'-dimethylcarbamoyl)hydroxy-1-(1-naphtylmethyl)-2-pyridinemethylene]hydroxylamine chloride, O-(p-methoxybenzyl)-N-[5-(N',N'-dimethylcarbamoyl)hydroxy-1-(2-methyl-1-naphtylmethyl)-2-pyridinemethylene]hydroxylamine chloride, O-(p-methoxybenzyl)-N-[5-(N',N'-dimethylcarbamoyl)hydroxy-1-diphenylmethyl-2-pyridinemethylene]hydroxylamine chloride, O-(p-methoxybenzyl)-N-[5-(N',N'-dimethylcarbamoyl)hydroxy-1-(2-hydroxy-4-nitrobenzyl)-2-pyridinemethylene]hydroxylamine chloride, O-(p-methoxybenzyl)-N-[5-(N',N'-dimethylcarbamoyl)hydroxy-1-(p-carboxybenzyl)-2-pyridinemethylene]hydroxylamine chloride, O-(p-methoxybenzyl)-N-[5-(N',N'-dimethylcarbamoyl)hydroxy-1-(p-cyanobenzyl)-2-pyridinemethylene]hydroxylamine chloride can be made by the same procedure replacing 3-hydroxy-2-pyridine aldehyde with 2-formyl-5-hydroxy pyridine.

EXAMPLE 9

Preparation of
N-[5-(N',N'-Dimethylcarbamoyl)hydroxy-1-methyl-2-pyridine methylene]hydroxylamine chloride (2d)

2-Formyl-5-hydroxypyridine. To a stirred solution of 21.8 g of 5-hydroxy-2-picoline (0.2 mol) in 200 mL of glacial acetic acid was added 18 mL of 30% hydrogen peroxide (0.159 mol) in one portion. The mixture was heated in an oil bath at 80°–85° C. with stirring for 3 h. Then another 18 mL of hydrogen peroxide was added and the mixture was stirred for 3 h at the same temperature. Excess solvent was removed in vacuo followed by the addition of acetone, which caused the pyridine N-oxide to crystallize. Without further purification, 200 mL of acetic anhydride was added to the solid and the mixture was heated at 120° C. with stirring in an oil bath for 2 h. After cooling to room temperature, excess acetic anhydride was removed by high vacuum distillation. The oily material was again oxidized with 30% hydrogen peroxide twice and rearranged with acetic anhydride following the same procedure and amounts depicted above. The black oily material obtained was hydrolyzed with 200 mL of 1N HCl (0.2 mol) at room temperature for 3 weeks (hydrolysis at higher temperature may be harmful to the pyridine nucleus). The mixture was neutralized with anhydrous sodium carbonate, indicated by litmus paper and then extracted three times with 300 mL of diethylether. The combined ether extracts were dried ($MgSO_4$), filtered and evaporated to leave a solid material in a small amount of oil. The pure product (7.8 g, 32%) was obtained by filtering the solid, followed by washing it with a small amount of ether. It is yellow in color and shows a sharp melting point at 186°–187° C. $^1$H NMR ($d_6$-DMSO) δ: 11.10 (br. s, 1H, OH); 9.87 (s, 1H, CHO); 8.35 (d, J=2 Hz, 1H); 7.58 (d, J=9 Hz, 1H); 7.35 (d of d, J=2 Hz, 9 Hz, 1H).

N-(5-Hydroxy-2-pyridinemethylene) hydroxylamine. To 200 mL of 2.5% (w/w) sodium hydroxide solution was dissolved 5.5 g of 5-hydroxy-2-formylpyridine (45 mmol). Subsequently 12.5 g of hydroxylamine HCl (180 mmol) was added to the solution in one portion. The solution turned cloudy after being stirred for 10 minutes. After stirring at room temperature for 3 h, the precipitate was filtered under vacuum and dried in the air for several days to yield 4.8 g of N-(5-hydroxy-2-pyridinemethylene) hydroxylamine (78%). The solid is of white and decomposes at 195° C. $^1$H NMR ($d_6$-DMSO) δ: 11.27 (br. s, 1H); 10.83 (br. s, 1H); 8.18 (d, J=2 Hz, 1H); 8.05 (s, 1H, CH=N); 7.72 (d, J=9 Hz, 1H); 7.25 (d of d, J=2 Hz, 9 Hz, 1H).

N-[5-(N',N'-Dimethylcarbamoyl)hydroxy-2-pyridine methylene]hydroxylamine. Dimethylcarbamoyl chloride (5.2 mL, 57 mmol) was added to a solution of N-(5-hydroxy-2-pyridinemethylene) hydroxylamine (6.53 g, 47 mmol) in 40 mL of pyridine. It was stirred at room temperature overnight and then the solvent was removed in vacuo, leaving a light green paste. The paste was dissolved in a minimum quantity of acetone and then triturated with ethyl acetate and placed in the freezer overnight. Glassy needles formed and were filtered and washed with ethyl acetate to yield 3.0 g of pure product (30%), m.p. 134°–135° C.

N-[5-(N',N'-Dimethylcarbamoyl)hydroxy-1-methyl-2-pyridinemethylene]hydroxylamine chloride. Methyl iodide (5.3 mL, 85 mmol) was added to a solution of N-[5-(N',N'-dimethylcarbamoyl)hydroxy-2-pyridine methylene]hydroxylamine (2.8 g, 13.4 mmol) in 25 mL of acetonitrile. The resulting mixture was put into a glass pressure vessel and heated at 80° C. for 3 days. The solvent was removed in vacuo and the residue was dissolved in a minimum quantity of acetone, triturated with ether and placed in the freezer overnight. A dark yellow solid resulted and was filtered under vacuum and washed with 1:1 ether/acetone to yield 3.25 g of the iodide salt. Freshly made AgCl (2 eq, washed well with water) was added to the iodide salt in acetonitrile/water (60 mL/100 mL) and stirred for several hours. After filtration, the residue was crystallized from acetone/ether and dried in the air for several days to yield 2.5 g of the chloride salt (monohydrate, 72% yield); m.p. 159°–160° C. $^1$H NMR ($d_6$-DMSO) δ: 9.18 (s, 1H); 8.65 (s, 1H); 8.40 (d of d, 2H, J=2 Hz, 9 Hz); 4.36 (s, 3H); 3.3 (s, $H_2O$); 3.1 (s, 3H); 2.95 (s, 3H). Anal. Calcd. for $C_{10}H_{14}N_3O_3Cl·H_2O$: C, 43.25; H, 5.81; N, 15.13; Cl, 12.76. Found: C, 43.42; H, 5.81; N, 15.09; Cl, 12.87.

N-[3-(N',N'-Dimethylcarbamoyl)hydroxy-1-methyl-2-pyridinemethylene]hydroxylamine chloride can be made by the same procedure replacing 2-formyl-5-hydroxypyridine with 3-hydroxy-2-pyridine carbaldehyde.

EXAMPLE 10

Preparation of
2-[[(Aminocarbonyl)hydrazono]methyl]-3-hydroxy-1-methyl pyridinium chloride (3a)

2-[[(Aminocarbonyl)hydrazono]methyl]-3-hydroxy pyridine. Sodium acetate (2.21 g, 16 mmol) was dissolved in 25 mL of water and then semicarbazide hydrochloride was added (1.81 g, 16 mmol), followed by 3-hydroxy-2-pyridine aldehyde (2.0 g, 16 mmol). The resulting mixture was stirred at room temperature for 2 h. The solid in the reaction mixture was then filtered, washed with water and dried to yield 2.71 g (93%) of the semicarbazone. It was used in the next step without further purification; m.p.: 215°–217° C. (dec.).

2-[[(Aminocarbonyl)hydrazono]methyl]-3-hydroxyl-1methyl pyridinium iodide. A glass pressure tube containing a stirring bar was charged with 20 grams (11.1 mmoles) of 2-[[(aminocarbonyl)hydrazono]methyl]-3-hydroxy pyridine, 2.5 g of barium carbonate, 7.0 g (49.3 mmol) of methyl iodide and 30 mL of DMF. The reaction mixture was stirred for two days at 65° C. in an oil bath. After that time the solvent was removed in vacuo, the residue shaken with 50 mL of warm water and filtered. The filtrate was then treated with an aqueous solution of $H_2SO_4$ in amount needed for the precipitation of $Ba^{2+}$ present in the solution. After collecting $BaSO_4$, the filtrate was concentrated and crystallized from a mixture of water and ethanol to afford 2.1 g (58.3%) of the methiodide salt, m.p. 180°–182° C.

2-[[(Aminocarbonyl)hydrazono]methyl]-3-hydroxy-1-methyl pyridinium chloride. The preceeding iodide, 6.0 grams (18.6 mmol) was dissolved in 150 mL of water and stirred with silver chloride precipitated from a solution of 6.0 g (35.3 mmol) of silver nitrate with excess of aqueous HCl. After 40 min the reaction mixture was filtered and the precipitate washed with a total of 100 mL of warm water. Pale yellow crystals of product melting at 230°–232° C. (dec.) were obtained from the combined filtrate by both rotoevaporation and precipitation with acetone. Yield 4.12 grams (95.3%). $^1$H NMR ($D_2O$, TSP) δ: 8.45 (s, 1H), 8.36 (d, 1H, J=5.8 Hz), 8.03 (d, 1H, J=8.3 Hz), 7.80 (d of d, 1H), 4.42 (s, Me). Anal.

Calcd for $C_8H_{11}N_4O_2Cl$: C, 41.66; H, 4.81; N, 24.28; Cl, 15.37. Found C, 41.59, H, 4.85; N, 24.28; Cl, 15.44.

2-[[(Aminothiocarbonyl)hydrazono]methyl]-3-hydroxy-1-methyl pyridinium chloride, 2-hydrazonomethyl-3-hydroxy-1-methyl pyridinium chloride, 1-methyl-2-(3-hydroxy-1-methyl-2-pyridinemethylene) hydrazine chloride, 1-methyl-1-phenyl-2-(3-hydroxy-1-methyl-2-pyridinemethylene) hydrazine chloride, 1,1-diphenyl-2-(3-hydroxy-1-methyl-2-pyridinemethylene) hydrazine chloride, 1-(2,4-dinitrophenyl)-2-(3-hydroxy-1-methyl-2-pyridinemethylene) hydrazine chloride, and 1-(2-naphtyl)-2-(3-hydroxy-1-methyl-2-pyridinemethylene) hydrazine chloride can be made by the same procedure replacing semicarbazide in the above example respectively with thiosemicarbazide, hydrazine, methylhydrazine, 1-methyl-1-phenylhydrazine, 1,1-diphenylhydrazine, 2,4-dinitrophenylhydrazine, and 2-naphtylhydrazine. 2-[[(Aminocarbonyl)hydrazono]methyl]-5-hydroxy-1-methyl pyridinium chloride, 2-[[(aminothiocarbonyl)hydrazono]methyl]-5-hydroxy-1-methyl pyridinium chloride, 2-hydrazonomethyl-5-hydroxy-1-methyl pyridinium chloride, 1-methyl-2-(5-hydroxy-1-methyl-2-pyridinemethylene) hydrazine chloride, 1-methyl-1-phenyl-2-(5-hydroxy-1-methyl-2-pyridinemethylene) hydrazine chloride, 1,1-diphenyl-2-(5-hydroxy-1-methyl-2-pyridinemethylene) hydrazine chloride, 1-(2,4-dinitrophenyl)-2-(5-hydroxy-1-methyl-2-pyridinemethylene) hydrazine chloride, and 1-naphtyl-2-(5-hydroxy-1-methyl-2-pyridinemethylene) hydrazine chloride can be made by the same procedure replacing 3-hydroxy-2-pyridine aldehyde with 2-formyl-5-hydroxy pyridine. 2-Hydrazonomethyl-3-hydroxy-1,6-dimethyl pyridinium chloride, 1-methyl-2-(1,6-dimethyl-3-hydroxy-2-pyridinemethylene) hydrazine chloride, 1-methyl-1-phenyl-2-(1,6-dimethyl-3-hydroxy-2-pyridinemethylene) hydrazine chloride, and 1,1-diphenyl-2-(1,6-dimethy-3-hydroxy-2-pyridinemethylene) hydrazine chloride can be made by the same procedure replacing 3-hydroxy-2-pyridine aldehyde in the above example with 3-hydroxy-6-methyl-2-pyridine aldehyde.

EXAMPLE 11

Preparation of 3-Hydroxy-1-methyl-2-[[(N-phenylaminocarbonyl)hydrazono]methyl]pyridinium chloride (3b)

3-Hydroxy-2-[[(N-phenylaminocarbonyl)hydrazono]methyl]pyridine. 4-Phenyl semicarbazide (4.91 g, 33 mmol) was added to a suspension of 3-hydroxy-2-pyridine carbaldehyde (4.0 g, 33 mmol) in a mixture of ethanol water (30 mL: 40 mL). The reaction mixture was stirred at room temperature for 3 h and the yellow product was collected by filtration. The yellow precipitate was washed with EtOH/H$_2$O 1:1 and dried under P$_2$O$_5$ to yield 8.22 g (99%) of product. It can be recrystallized from EtOH/H$_2$O; m.p. 201°-2° C. (dec.). $^1$H NMR (d$_6$-DMSO) δ: 10.85 (br.s., 1H); 10.6 (br.s., 1H); 9.14 (s, 1H); 8.27 (s, 1H); 8.15 (d of d, 1H); 7.55 (d, 2H); 7.26-7.36 (m, 4H); 7.01 (t, 1H).

3-Hydroxy-2-[[(N-phenylaminocarbonyl)hydrazono]methyl]-1-methyl pyridinium chloride. Methyl iodide (7.2 mL, 0.12 mol) was added to a suspension of 2-[[(N-phenylaminocarbonyl) hydrazono]methyl]-3-hydroxy pyridine (3.72 g, 15 mmol) in 50 mL of acetonitrile. The reaction mixture was placed in two pressure glass vessels and heated at 70° C. for 3 days. The solid which filled the reaction flasks was filtered and triturated well with warm (40° C.) acetone. The product was dried to yield 5.13 g (89%) of methiodide. It was dissolved in a mixture of water/acetonitrile (500 mL: 300 mL) and then freshly made AgCl (2 eq) was added. The suspension was stirred at room temperature for 2 h and then filtered through Celite. The filtrate was concentrated to dryness in vacuo and the residue was triturated with acetone. The yellow solid was filtered, washed with acetone and dried to yield 3.67 g (93%) of the pure chloride; m.p. 220°-221° C. (dec.). It can be recrystallized from EtOH. $^1$H NMR (d$_6$-DMSO) δ: 11.74 (br.s., 1H); 9.27 (s, 1H); 8.58 (d, 1H, J=5.7 Hz); 8.39 (s, 1H); 8.17 (d, 1H, J=8.2 Hz); 7.85 (d of d, 1H, J=5.7 Hz, J=8.2 Hz); 7.57 (d, 2H, J=7.6 Hz); 7.31 (t, 2H, J=7.6 Hz); 7.04 (t, 1H, J=7.6 Hz); 4.48 (s, 3H). Anal. Calcd. for $C_{14}H_{15}ClN_4O_2 \times 0.95$ H$_2$O: C, 51.90; H, 5.26; N, 17.29; Cl, 10.94. Found: C, 51.90; H, 5.22; N, 17.36; Cl, 10.89.

3-Hydroxy-1-methyl-2-[[(N-phenylaminothiocarbonyl)hydrazono]methyl]pyridinium chloride, 2-[[(N,N-diphenylaminocarbonyl)hydrazono]methyl]-3-hydroxy-1-methyl pyridinium chloride, 2-[[(N,N-dimethylaminothiocarbonyl)hydrazono]methyl]3-hydroxy-1-methyl pyridinium chloride, 2-[[(N-ethylaminothiocarbonyl)hydrazono]methyl]-3-hydroxy-1-methyl pyridinium chloride, 3-hydroxy-1-methyl-2-[[(N-naphtylaminocarbonyl) hydrazono]methyl]pyridinium chloride, and 2-[[[N-(1-chloro-2-naphtyl)amino carbonyl]-hydrazono]methyl]-3-hydroxy-1-methyl pyridinium chloride can be made by the same procedure replacing 4-phenylsemicarbazide in the above example respectively with 4-phenyl-3-thiosemicarbazide, 4,4-diphenylsemicarbazide, 4,4-dimethyl-3-thiosemicarbazide, 4-ethyl-3-thiosemicarbazide, 4-(2-naphtyl)semicarbazide and 4-(1-chloro-2-naphtyl)semicarbazide. 5-Hydroxy-1-methyl-2-[[(N-phenylaminothiocarbonyl)hydrazono]methyl]pyridinium chloride, 5-hydroxy-1-methyl-2-[[(N-phenylaminothiocarbonyl) hydrazono]methyl]pyridinium chloride, 2-[[(N,N-diphenylaminocarbonyl)hydrazono]methyl]-5-hydroxy-1-methyl pyridinium chloride, 2-[[(N,N-dimethylaminothiocarbonyl) hydrazono]methyl]-5-hydroxy-1-methyl pyridinium chloride, 2-[[(N-ethylaminothiocarbonyl) hydrazono]methyl]-5-hydroxy-1-methyl pyridinium chloride, 5-hydroxy-1-methyl-2-[[(N-naphtylaminocarbonyl)hydrazono]methyl]pyridinium chloride, and 2-[[[N-(1-chloro-2-naphtyl)amino carbonyl]hydrazono]methyl]-5-hydroxy-1-methyl pyridinium chloride can be made by the same procedure replacing 3-hydroxy-2-pyridine aldehyde with 2-formyl-5-hydroxy pyridine.

EXAMPLE 12

Preparation of 1-Methyl-2-[[(N-phenylaminocarbonyl) hydrazono]methyl]pyridinium chloride (3d)

2-[[(N-Phenylaminocarbonyl)hydrazono]methyl]-pyridine. Pyridine-2-Aldehyde (5.7 mL, 0.06 mol) was added to a suspension of sodium acetate (4.92 g, 0.06 mol) and semicarbazide (9.07 g, 0.06 mol) in 60 mL of water. The resulting mixture was stirred at room temperature for 14 h and the solid in suspension was filtered and washed thoroughly with water. After drying, the semicarbazone was obtained as a dark beige solid (12.54 g, 87%) and was used in the next step without further purification; m.p. 181°-182° C.

1-Methyl-2-[[(N-phenylaminocarbonyl)hydrazono]methyl]pyridinium chloride. 2-[[(N-Phenylaminocarbonyl)hydrazono]methyl]pyridine (4.47 g, 0.02 mol) was divided into two pressure glass tubes and dissolved in acetonitrile (20 mL each). Methyl iodide was then added (2.6 mL each, 0.04 mol), the tubes were tightly closed and heated at 65° C. for 3 days. The reaction flasks were cooled to 10°-15° C. and the solid was filtered. The yellow solid was washed with acetone and ether and dried to yield 6.66 g (92%) of the iodide salt; m.p. 192°-193° C. (dec.). It was dissolved in 400 mL of acetonitrile/water 1:1 and exchanged with freshly made AgCl (from 5.92 g of AgNO$_3$ and excess conc. HCl, washed well with water). The resulting suspension was stirred at room temperature for 2 h. The silver iodide was filtered off and the filtrate was concentrated to dryness in vacuo to yield a yellow solid that was triturated with acetone and ether. It was filtered and dried to yield 4.86 (96%) of the pure chloride salt as a yellow solid; m.p. 187°-188° C. (dec.). $^1$H NMR (d$_6$-DMSO) δ: 11.87 (s, 1H); 9.45 (s, 1H); 8.98 (d of d, 2H); 8.56 (t, 1H); 8.43 (s, 1H); 8.01 (t, 1H); 7.62 (d, 2H); 7.34 (t, 2H); 7.08 (t, 1H); 4.36 (s, 3H). Anal. Calcd. for C$_{14}$H$_{15}$ClN$_4$O x 0.48 H$_2$O: C, 56.15; H, 5.37; N, 18.71; Cl, 11.84. Found: C, 56.15; H, 5.38; N, 18.69; Cl, 11.88.

EXAMPLE 13

Preparation of
2-[[(Aminocarbonyl)hydrazono]methyl]-3-(N,N-dimethylcarbamoyl)hydroxy-1-methyl pyridinium chloride
(4a)

2-[[(Aminocarbonyl)hydrazono]methyl]-3-hydroxy pyridine. Sodium acetate (2.21 g, 16 mmol) was dissolved in 25 mL of water and then semicarbazide hydrochloride was added (1.81 g, 16 mmol), followed by 3-hydroxy-2-pyridine aldehyde (2.0 g, 16 mmol). The resulting mixture was stirred at room temperature for 2 h. The solid in the reaction mixture was then filtered, washed with water and dried to yield 2.71 g (93%) of the semicarbazone. It was used in the next step without further purification; m.p.: 215°-217° C. (dec.).

2-[[(Aminocarbonyl)hydrazono]methyl]-3-(N,N-dimethylcarbamoyl)hydroxy pyridine. The semicarbazone obtained in the previous step (2.71 g, 15 mmol) was suspended in 20 mL of pyridine and then N,N-dimethylcarbamyl chloride was added (4.2 mL, 45 mmol). The reaction flask was sealed with a septum and the mixture was stirred at room temperature for 20 h. The reaction mixture becomes a clear solution after one hour and the product begins to come out of solution after 2 h. When the reaction is complete, the mixture is cooled to 5°-10° C. in ice bath and filtered. The beige solid that results is washed with acetone/ether 1:1 and dried to yield 3.63 g (96%) of the carbamate which is used in the next step without further purification; m.p. 182°-3° C. (dec).

2-[[(Aminocarbonyl)hydrazono]methyl]-3-(N,N-dimethylcarbamoyl)hydroxy-1-methyl pyridinium chloride. The carbamate obtained in the previous step (3.63 g, 14 mmol) was dissolved in 50 mL hot (90° C.) DMF. When a clear solution was obtained, the reaction flask was cooled under running water until the inner temperature reached 26° C. Methyl iodide (6.3 mL, 100 mmol) was then added and the reaction mixture was left at 65° C. in a Parr shaker for 3 days. The solvent was removed in vacuo to yield a dark viscous residue which was triturated with acetone. The yellow solid that resulted was washed with acetone/ether 1:1, then with ether and dried to yield 5.15 g (94%) of the methiodide. Freshly made AgCl (from 4.45 g AgNO$_3$ and excess conc. HCl) was washed well with water and added to a solution of the methiodide (5.15 g, 13 mmol) in 200 mL acetonitrile/water 1:1. The resulting suspension was stirred at room temperature for 1.5 h. The silver iodide was filtered through Celite and the filtrate was concentrated to dryness in vacuo to yield a residue which is triturated with acetone. The resulting solid is filtered and recrystallized from CH$_3$CN/EtOH and acetone to yield 2.44 g (62%) of the pure chloride salt; m.p. 194°-195° C. (dec.). Anal. Calcd. for C$_{11}$H$_{16}$ClN$_5$O$_3$x 0.96 H$_2$O: C, 41.42; H, 5.66; N, 21.96; Cl, 11.12. Found: C, 41.42; H, 5.72; N, 21.81; Cl, 11.20.

2-[[(Aminocarbonyl)hydrazono]methyl]-3-(N,N-dimethylcarbamoyl)hydroxy-1,6-dimethyl pyridinium chloride can be made by the same procedure replacing 3-hydroxy-2-pyridine aldehyde in the above example with 3-hydroxy-6-methyl-2-pyridine aldehyde. 2-[[(Aminocarbonyl)hydrazono]methyl]-5-(N,N-dimethylcarbamoyl)hydroxy-1-methyl pyridinium chloride can be made by the same procedure replacing 3-hydroxy-2-pyridine aldehyde in the above example with 2-formyl-5-hydroxy pyridine.

EXAMPLE 14

Preparation of
3-(N,N-Dimethylcarbamoyl)hydroxy-1-methyl-2-[[(N-phenylaminocarbonyl) hydrazono]methyl] pyridinium chloride (4b)

3-(N,N-Dimethylcarbamoyl)hydroxy-2-[[(N-phenylaminocarbonyl)hydrazono]methyl] pyridine was prepared by reaction of dimethylcarbamyl chloride (16 mL, 0.18 mol) with 3-hydroxy-2-[[(N-phenylaminocarbonyl)hydrazono]methyl] pyridine (4.5 g, 17.5 mmol) in 30 mL of pyridine. The resulting mixture was stirred at room temperature for 6 h and poured over 500 mL of crushed ice. The beige precipitate was collected, washed thoroughly with water and dried to yield 5.48 g (95%) of product, m.p. 178°-180° C. The product (5.48 g, 16.7 mmol) was dissolved in acetonitrile/DMF and then methyl iodide (2.78 mL, 44.7 mmol × 3 vessels) was added to the reaction vessel. The resulting mixture was stirred at 70° C. for 3 days and cooled in a water-ice bath for 30 min. The precipitate was collected by filtration, washed with acetone/ether 1:1 and dried to yield 6.42 g (82%) of the methiodide salt. It was dissolved in 500 mL H$_2$O and 300 mL acetonitrile and then freshly made AgCl (2 eq, washed well with water) was added. The resulting suspension was stirred at room temperature for 2 h. It was filtered through Celite and the filtrate was concentrated to dryness in vacuo to a crisp yellow foam that becomes a yellow solid after trituration with acetone. The yellow solid was filtered, washed with ether and dried to yield 4.83 g (93%) of pure product as the chloride salt; m.p. 176°-177° C. (dec.). Anal. Calcd. for C$_{17}$H$_{20}$ClN$_5$O$_3$ $_x$ 0.84 H$_2$O: C, 51.95; H, 5.56; N, 17.82; Cl, 9.02. Found: C, 51.95; H, 5.55; N, 17.80; Cl, 9.11.

5-(N,N-Dimethylcarbamoyl)hydroxy-1-methyl-2-[[(N-phenylaminocarbonyl) hydrazono]methyl] pyridinium chloride can be made by the same procedure replacing 3-hydroxy-2-pyridine aldehyde with 2-formyl-5-hydroxy pyridine.

EXAMPLE 15

Preparation of
2-(3-Hydroxy-1-methyl-2-pyridinemethylene)-1-[2(1-pyridinium)acetyl]hydrazine dichloride (5a)

2(3-Hydroxy-2-pyridinemethylene)-1-[2-pyridinium)acetyl] hydrazine chloride. 1-(Carboxymethyl) pyridinium chloride hydrazide (2.63 g, 0.014 mol) in 10 mL of methanol was added to a solution of 2-aldehyde-3-hydroxy pyridine (1.72 g, 0.014 mol) in 20 mL of $CH_3CN$. The resulting dark yellow solution is stirred at room temperature for 2 h and at the end of this period a beige solid filled the reaction mixture. Ethyl ether was added (10 mL) and the reaction mixture was cooled to 5°-10° C. before filtering the beige precipitate. The solid was washed with ethyl ether and dried to yield 3.72 g (91%) of product; m.p. 229°-30° C. (dec).

2-(3-Hydroxy-1-methyl-2-pyridinemethylene)-1-[2-(1-pyridinium)acetyl] hydrazine dichloride. The acyl hydrazone obtained in the previous step (3.5 g, 0.012 mol) was divided into three pressure glass vessels and each portion was dissolved in 20 mL of acetonitrile. Methyl iodide was added to these solutions (1.2 mL each, 0.02 mol) and the resulting mixtures were heated at 70° C. for 3 days. The reaction mixtures were concentrated in vacuo to a dark residue which was triturated with acetone/ethanol 5:1. The resulting yellow solid was washed with acetone/ethanol 5:1 and dried to obtain 4.39 g (84%) of the iodide salt, m.p. 193°-94° C. (dec). Freshly made AgCl (from 3.43 g of $AgNO_3$ and excess conc. HCl) was washed well with water and added to a solution of the iodide salt (4.39 g, 0.01 mol) in 300 mL acetonitrile/water 1:1. The resulting suspension was stirred at room temperature for 2 h. The silver iodide was filtered through Celite and the filtrate was concentrated to dryness in vacuo to yield a solid that was triturated with acetone. The dark beige solid was filtered, washed with acetone and dried to yield 2.89 g (84%) of pure product as the chloride salt; m.p. 230°-31° C. (dec.). Anal. Calcd. for $C_{14}H_{16}Cl_2N_4O_2$ x 0.96 $H_2O$: C, 46.65; H, 5.01; N, 15.55; Cl, 19.67. Found: C, 46.65; H, 4.95; N, 16.33; Cl, 20.66.

2-(3-Hydroxy-1-methyl-2-pyridinemethylene)-1-[2-(trimethylammonium)acetyl]hydrazine dichloride, 1-[2-(4-chloro-1-pyridinium)acetyl]-2-(3-hydroxy-1-methyl-2-pyridinemethylene) hydrazine dichloride, 1-[2-(3-carboxy-1-isoquinolinium)acetyl]-2-(3-hydroxy-1-methyl-2-pyridinemethylene) hydrazine dichloride, 1-[2-(2-carboxy-4-methoxy-1-quinolinium) acetyl]-2-(3-hydroxy-1-methyl-2-pyridinemethylene) hydrazine dichloride, 2-(3-hydroxy-1-methyl-2-pyridinemethylene)-1-[2-(3-hydroxy-1-pyridinium)acetyl] hydrazine dichloride, 2-(3-hydroxy-1-methyl-2-pyridinemethylene)-1-[2-(2-methyl-1-piperidinium) acetyl] hydrazine dichloride can be made by the same procedure replacing 1-(carboxymethyl) pyridinium chloride hydrazide respectively with (carboxymethyl)trimethylammonium chloride hydrazide (Girard's reagent "T"), 4-chloro-1-(carboxymethyl)pyridinium chloride hydrazide, 3-carboxy-1-(carboxymethyl)isoquinolinium chloride hydrazide, 2-carboxy-4-methoxy-1-(carboxymethyl)quinolinium chloride hydrazide, 3-hydroxy-1-(carboxymethyl)-pyridinium chloride hydrazide, and 1-methyl-1-(carboxymethyl) piperidinium chloride hydrazide. 2-(5-Hydroxy-1-methyl-2-pyridinemethylene)-1-[2-(1-pyridinium)acetyl] hydrazine dichloride, 2-(5-hydroxy-1-methyl-2-pyridinemethylene)-1-[2-(trimethylammonium)acetyl] hydrazine dichloride, 1-[2-(4-chloro-1-pyridinium)acetyl]-2-(5-hydroxy-1-methyl-2-pyridinemethylene) hydrazine dichloride, 1-[2-(3-carboxy-1-isoquinolinium)acetyl]-2-(5-hydroxy-1-methyl-2-pyridinemethylene) hydrazine dichloride, 1-[2-(2carboxy-4-methoxy-1-quinolinium)acetyl]-2-(5-hydroxy-1-methyl-2-pyridinemethylene) hydrazine dichloride, 2-(5-hydroxy-1-methyl-2-pyridinemethylene)-1-[2-(3-hydroxy-1-pyridinium)acetyl] hydrazine dichloride, and 2-(5-hydroxy-1-methyl-2-pyridinemethylene)-1-[2-(1-piperidinium)acetyl] hydrazine dichloride can be made by the same procedure replacing 3-hydroxy-2-pyridine aldehyde with 2-formyl-5-hydroxy pyridine.

EXAMPLE 16

Preparation of 2-(1-Methyl-2-pyridinemethylene)-1-[2-(1-pyridinium)acetyl] hydrazine dichloride (5b)

2-(2-pyridinemethylene)-1-[2-(1-pyridinium)acetyl] hydrazine chloride. 1-(Carboxymethyl) pyridinium chloride hydrazide (5.25 g, 28 mmol) and pyridine-2-carbaldehyde (2.7 mL, 28 mmol) were dissolved in 25 mL acetonitrile: methanol (4:1). The resulting mixture was stirred at room temperature for 2 h, with the product beginning to come out of solution after 20 min of reaction. After 2 h the white solid in the reaction mixture was filtered and washed with acetonitrile and ether. After drying, the product was obtained as a white solid (5.27 g, 68%) and was used in the next step without further purification; m.p. 240°-241° C.(dec.). $^1H$ NMR ($d_6$-DMSO) δ: 12.43 (br.s., 1H); 9.07 (d, 2H); 8.70 (t, 1H); 8.66 (d, 1H); 8.24 (d of d, 2H); 8.19 (s, 1H); 8.01-7.90 (m, 2H); 7.48-7.44 (m, 1H); 6.07 (s, 2H).

2-(1-Methyl-2-pyridinemethylene)-1-[2-(1-pyridinium)acetyl] hydrazine dichloride. The acyl hydrazone obtained in the previous step (2.88 g, 10 mmol) was divided into two pressure vessels and each portion was dissolved in 25 mL of DMF. Methyl iodide was added to these solutions (1.62 mL each, 25 mmol) and the resulting mixtures were heated at 70° C. for 3 days. The solvent was removed in vacuo to yield a dark residue which was triturated with acetone. The resulting solid was filtered, washed with acetone and ether and dried to yield 4.25 g (quantitative) of the methiodide as a yellow solid. Freshly made AgCl (from 3.77 g $AgNO_3$ and excess conc. HCl) was washed well with water and added to a solution of the iodide salt (4.18 g, 10 mmol) in 200 mL acetonitrile/water 1:1. The resulting suspension was stirred at room temperature for 1.5 h. The silver iodide was filtered through Celite and the filtrate was concentrated to dryness in vacuo to yield 3.63 g of a yellow solid. Recrystallization from ethanol/acetone affords the pure chloride as a beige solid (3.0 g, 92%); m.p. 209°-210° C. (dec). $^1H$ NMR ($d_6$-DMSO) δ: 9.13 (d, 2H); 9.08 (d, 2H); 8.75-8.59 (m, 4H); 8.26 (t, 2H); 8.10 (m, 1H); 6.19 (br.s., 2H); 4.42 (s, 3H). Anal. Calcd. for $C_{14}H_{16}Cl_2N_4O$ x 0.91 $H_2O$: C, 48.94; H, 5.23; N, 16.31; Cl, 20.64. Found: C, 48.94; H, 5.25; N, 16.31; Cl, 20.43.

EXAMPLE 17

Preparation of O-Diphenylmethyl-N-(3-hydroxy-1-methyl-2-pyridinemethylene) Hydroxylamine Iodide O-Diphenylmethyl-N-(3-hydroxy-2-pyridinemethylene) hydroxylamine. O-Diphenyl methyl hydroxylamine hydrochloride (3.35 g, 14.2 mmol) was added to a solution of NaOH (0.57 g, 14.2 mmol) in 10 mL of $H_2O$. After the addition of 10 mL of EtOH, 3-hydroxy-2-pyridine aldehyde (1.75 g, 14.2 mmol) was added. The mixture was heated on a steam bath for 1 h. While the solution was allowed to cool an additional 30 mL of $H_2O$ was added. The product precipitated out as yellow needles. The mixture was filtered to isolate the pure product (3.8 g, 89%), m.p. 83°-84° C. $^1H$ NMR (CDCl$_3$) δ: 9.57 (s, 1H); 8.40 (s, 1H); 7.33 (s, 10H); 7.13 (m, 3H); 6.23 (s, 1H). Anal. Calcd. for C$_{19}$H$_{16}$N$_2$O$_3$: C, 74.97; H, 5.31; N, 9.21. Found: C, 74.88; H, 5.32; N, 9.17.

O-Diphenylmethyl-N-(3-hydroxy-1-methyl-2-pyridinemethylene) hydroxylamine iodide. A solution of O-diphenylmethyl-N-(3-hydroxy-2-pyridinemethylene) hydroxylamine (1.0 g, 3.29 mmol) in 45 mL of EtOH was placed in a glass pressure tube. Methyl iodide (0.9 mL, 13.8 mmol) was then added, and the tube was sealed tightly. The tube was heated at 69° C. in an oil bath for 20 h. The solvent was removed in vacuo, and the residue was triturated with acetone to give the product as a shiny dark yellow solid (1.4 g, 95%), m.p. 163°–165° C. The chloride salt can be obtained as described above.

EXAMPLE 18

Preparation of
O-Benzyl-N-(1,6-dimethyl-3-hydroxy-2-pyridinemethylene) Hydroxylamine Chloride 3-Hydroxy-6-methyl-2-pyridine carbaldehyde. 3-Hydroxy-6-methyl-2-pyridine methanol (20.0 g, 0.14 mol) and selenium dioxide (8.0 g, 72 mmol) were dissolved in 140 mL of 1,4-dioxane and 280 mL of absolute ethanol. The resulting mixture was heated at 80°–85° C. for 12 h. The selenium precipitate was removed by filtration and the filtrate was concentrated to dryness in vacuo. The dark red residue was sublimed at 90° C. and 14 mmHg for 6 h to obtain 11.0 g (56%) of pure product, m.p. 101°–102° C.; $^1$H NMR (CDCl$_3$) δ: 10.50 (br s, 1H), 10.03 (s, 1H), 7.27 (s, 2H); 2.53 (s, 3H).

O-Benzyl-N-(3-hydroxy-6-methyl-2-pyridinemethylene) hydroxylamine. Sodium hydroxide (3.2 g, 0.08 mol) was dissolved in 80 mL of a 1:1 mixture of ethanol/water and then O-Benzylhydroxylamine hydrochloride (12.77 g, 0.08 mol) was added. The reaction mixture was stirred at room temperature and when a clear solution was obtained 11.0 g (0.08 mol) of 3-hydroxy-6-methyl-2-pyridine carbaldehyde was added and the resulting mixture was stirred at room temperature for 11 h. The reaction mixture was cooled in an ice bath and filtered to yield 18.53 g (96%) of product as a white solid, m.p. 81°–82° C. $^1$H NMR (Me$_2$SO-d$_6$) δ: 9.85 (br s, 1H), 8.40 (s, 1H), 7.30–7.47 (m, 5H), 7.22 (d, 1H), 7.13 (d, 1H), 5.22 (s, 2H), 2.36 (s, 3H).

O-Benzyl-N-(1,6-dimethyl-3-hydroxy-2-pyridinemethylene) hydroxylamine iodide. O-Benzyl-N-(3-hydroxy-6-methyl-2-pyridinemethylene) hydroxylamine (10.0 g, 0.04 mol) was dissolved in 75 mL of acetonitrile and 7.7 mL (0.12 mol) of methyl iodide. The reaction mixture was heated in a pressure glass vessel at 90° C. for 3 days. The solvent was removed in vacuo and the residue was triturated with acetone to yield 8.1 g of a yellow solid. Recrystallization from acetone/EtOH/Et$_2$O yields 5.5 g (35%) of pure product as a pale yellow solid, $^1$H NMR (Me$_2$SO-d$_6$) δ: 8.55 (s, 1H); 7.92 (d, 1H); 7.87 (d, 1H); 7.30–7.48 (m, 5H); 5.2,5.33 (s, 2H); 3.93,4.08 (s, 3H); 2.72 (s, 3H).

O-Benzyl-N-(1,6-dimethyl-3-hydroxy-2-pyridinemethylene) hydroxylamine chloride. O-Benzyl-N-(1,6-dimethyl-3-hydroxy-2-pyridinemethylene) hydroxylamine iodide (5.5 g, 14 mmol) were dissolved in 700 mL of water and 4.1 g (28 mmol) of freshly prepared AgCl (from silver nitrate and excess conc. HCl) was then added. The suspension was stirred mechanically for 2.5 h at room temperature and the silver iodide was then removed by filtration. The filtrate was concentrated to dryness in vacuo and the residue was triturated with acetone to yield 3.6 g (86%) of pure product as a light beige solid, m.p. 175°–6° C. (dec.). $^1$H NMR (Me$_2$SO-d$_6$) δ: 8.52, 8.06 (s, 1H); 8.10 (d, 1H); 7.85 (t, 1H); 7.30–7.45 (m, 5H); 5.30, 5.20 (s, 2H); 4.1, 3.9 (s, 3H); 2.69 (s, 3H). Anal. Calcd. for C$_{15}$H$_{17}$ClN$_2$O$_2$×0.15 H$_2$O: C, 60.96; H, 5.90; N, 9.48; Cl, 12.00. Found: C, 60.96; H, 5.90; N, 9.51; Cl, 12.02.

O-(1-Naphtylmethyl)-N-(1,6-dimethyl-3-hydroxy-2-pyridinemethylene) hydroxylamine chloride, O-(2-methyl-1-naphtylmethyl)-N-(1,6-dimethyl-3-hydroxy-2-pyridinemethylene) hydroxylamine chloride, O-methyl-N-(1,6-dimethyl-3-hydroxy-2-pyridinemethylene) hydroxylamine chloride, O-(p-chlorobenzyl)-N-(1,6-dimethyl-3-hydroxy-2-pyridinemethylene) hydroxylamine chloride, O-(p-cyanobenzyl)-N-(1,6-dimethyl-3-hydroxy-2-pyridinemethylene) hydroxylamine chloride, O-(2-hydroxy-4-nitrobenzyl)-N-(1,6-dimethyl-3-hydroxy-2-pyridinemethylene) hydroxylamine chloride, O-(p-methoxybenzyl)-N-(1,6-dimethyl-3-hydroxy-2-pyridinemethylene) hydroxylamine chloride, O-(p-dimethyl aminocarbonyloxybenzyl)-N-(1,6-dimethyl-3-hydroxy-2-pyridinemethylene) hydroxylamine chloride, O-(p-propylaminocarbonyl benzyl)-N-(1,6-dimethyl-3hydroxy-2-pyridine methylene) hydroxylamine chloride, O-benzyl-N-[3-(N',N'-dimethylcarbamoyl)hydroxy-1,6-dimethyl-2-pyridinemethylene]-hydroxylamine chloride, O-benzyl-N-[3-(N',N'-diethylcarbamoyl)hydroxy-1,6-dimethyl-2-pyridinemethylene]hydroxylamine chloride, O-benzyl-N-[3-(N',N'-difluoroethylcarbamoyl)hydroxy-1,6-dimethyl-2-pyridinemethylene]hydroxylamine chloride, O-(diphenylmethyl)-N-[3-(N',N'-dimethylcarbamoyl)hydroxy-1,6-dimethyl-2-pyridinemethylene]hydroxylamine chloride, O-(diphenylmethyl)-N-[1,6-dimethyl-3-(N'-isopropylcarbamoyl)hydroxy-2-pyridinemethylene]hydroxylamine chloride, O-(diphenylmethyl)-N-[3-[N'-(2-fluoroethyl)carbamoyl]hydroxy-1,6-dimethyl-2-pyridinemethylene]hydroxylamine chloride, O-(p-methoxybenzyl)-N-[3-(N',N'-dimethylcarbamoyl)hydroxy-1,6-dimethyl-2-pyridinemethylene]-hydroxylamine chloride, O-(p-methoxybenzyl)-N-[3-(N',N'-dimethylcarbamoyl)hydroxy-1-ethyl-6-methyl-2-pyridinemethylene]hydroxylamine chloride, O-(p-methoxybenzyl)-N-[3-(N',N'-dimethylcarbamoyl)hydroxy-1-benzyl-6-methyl-2-pyridinemethylene]hydroxylamine bromide, N-[3-(N',N'-dimethylcarbamoyl)hydroxy-1,6-dimethyl-2-pyridinemethylene]hydroxylamine chloride, 1,6-dimethyl-3-hydroxy-2-[[(N-phenylaminocarbonyl)hydrazono]methyl]pyridinium chloride, 1,6-dimethyl-3-hydroxy-2-[[(N-phenylaminothiocarbonyl) hydrazono]methyl]pyridinium chloride, 1,6-Dimethyl-2-[[(N,N-diphenylaminocarbonyl) hydrazono]methyl]-3-hydroxy pyridinium chloride, 2-(1,6-dimethyl-3-hydroxy-2-pyridinemethylene)-1-[2-(1-pyridinium)acetyl]hydrazine dichloride, 2-(1,6-dimethyl-3-hydroxy-2-pyridinemethylene)-1-[2-(trimethylammonium)acetyl]hydrazine dichloride, and 2-(1,6-dimethyl-3-hydroxy-2-pyridinemethylene)-1-[2-(4-chloro-1-pyridinium)acetyl]hydrazine dichloride can be made by the same procedure replacing 3-hydroxy-2-pyridine carbaldehyde with 3-hydroxy-6-methyl-2-pyridine carbaldehyde.

EXAMPLE 19

Preparation of O-Benzyl-N-(1-benzyl-3-hydroxy-2-pyridinemethylene) hydroxylamine bromide O-Benzyl-N-(3-hydroxy-2-pyridinemethylene) hydroxylamine. O-Benzyl hydroxylamine (10.4 g, 65 mmol) was added to a solution of NaOH (2.6 g, 65 mmol) in 66 mL of $H_2O$/EtOH 1:1. 3-Hydroxy-2-pyridine carbaldehyde (8.0 g, 65 mmol) was added to this solution and the resulting mixture was stirred at room temperature 3 h. The white precipitate was then filtered and dried to yield 13.3 g (90%) of pure product, m.p. 64°–65° C. $^1$H NMR (CDCl$_3$) δ: 9.72 (s, 1H); 8.37 (s, 1H); 8.13 (d of d,J=2Hz,J=4Hz, 1H); 7.33 (m, 7H); 5.17 (s, 2H).

O-Benzyl-N-(1-benzyl-3-hydroxy-2-pyridinemethylene) hydroxylamine bromide. Benzyl bromide (0.78 mL, 6.6 mmol) was added to a solution of O-benzyl-N-(3-hydroxy-2-pyridine methylene) hydroxylamine (1.0 g, 4.4 mmol) in 4 mL of acetonitrile. The resulting mixture was heated at 65° C. in a pressure bottle for 3 days. The solvent was removed in vacuo and coevaporated with water to leave an oily residue that was dissolved in 100 mL of water and treated with activated charcoal. This mixture was filtered through Celite and the filtrate was concentrated to dryness under high vacuum. Acetone (20 mL) was added to the residue and the product crystallized as light beige needles (1.5 g, 86%), m.p. 145°–146° C. $^1$H NMR (CDCl$_3$) δ: 8.68 (s, 1H); 8.63 (d of d, 1H); 8.52 (t, 1H); 7.69 (d of d, 1H); 7.35 (m, 8H); 7.10 (m, 2H); 6.12 (s, 2H); 5.25 (s, 2H). Anal. Calcd. for $C_{20}H_{19}BrN_2O_2$: C, 60.16; H, 4.80; N, 7.02; Br, 20.02. Found: C, 59.89; H, 4.86; N, 7.00; Br, 19.91.

O-Benzyl-N-(1-benzyl-5-hydroxy-2-pyridinemethylene) hydroxylamine bromide can be made by the same procedure replacing 3-hydroxy-2-pyridine aldehyde in the above example with 2-formyl-5-hydroxy pyridine.

TABLE I

Kinetic Constants for the Reversible Inhibition of Electric Eel and Human Erythrocyte Acetylcholinesterase.

| compd | $K_I$ (eel) μM | $K_I$ (human) μM | $IC_{50}$ (eel) μM | $IC_{50}$ (human) μM |
|---|---|---|---|---|
| 1a | 40 | 100 | 100 | 175 |
| 1b | 500 | >600 | | |
| 1c | | | NI[a] | NI[a] |
| 1d | | | 400 | >500 |
| 1e | | | 400 | >500 |
| 1f | | | NI[a] | NI[a] |
| 3a | | | 325 | 300 |
| 3b | 30, 340[b] | | | 240 |
| 4b | 85 | 100 | | |
| 5a | 10 | 20 | | |
| 5b | c | c | 40 | 40 |

[a]NI, no inhibition at concentrations up to 1 mM.
[b]Two distinct $K_I$'s with eel AChE, multiple binding with both enzymes.
[c]Multiple binding observed, only $IC_{50}$ values determined.

TABLE II

Kinetic Constants for the Irreversible Inhibition of Electric Eel and Human Erythrocyte Acetylcholinesterase.

| compd | $k_{obs}$/[I] (eel) ($M^{-1}s^{-1}$) | $k_{obs}$/[I] (human) ($M^{-1}s^{-1}$) | $K_I$ (eel) (μM) |
|---|---|---|---|
| 2a | 1700 | 68000 | NT[a] |
| 2b | 870 | 1100 | NT[a] |
| 2c | 5000 | >110000 | NT[a] |
| 4a | 25 | 2200 | 100 |
| Pyr[b] | 580[c] | 13000 | NT[a] |
| Phy[d] | 14000[c] | 19000 | NT[a] |

[a]NT, not tested (inhibition half-life is too short to measure accurately);
[b]Pyridostigmine: $k_{obs}$/[I] = 843 $M^{-1}s^{-1}$ (Forsberg, A. and Puu, G., Eur. J. Biochem. 1984, 140, 153.);
[d]Physostigmine: $k_{obs}$/[I] = 18500 $M^{-1}s^{-1}$ (Forsberg, A. and Puu, G., Eur. J. Biochem. 1984, 140, 153.).

TABLE III

In Vivo Evaluation of Pyridinium Derivatives as Intramuscular Pretreatment Agents Against GD in Mice.

| compd | $LD_{50}$ (μmol/kg) | time[a] (min) | dose[b] (μmol/kg) | % survival |
|---|---|---|---|---|
| 1a | 180 | 15/60 | 3.0–45 | 10–20 |
| 1b | >880 | 15/60 | 22 | 0/10 |
| 1d | >320 | 15/60 | 9.6 | 10/20 |
| 1e | >760 | 15/60 | 320/81 | 40/10 |
| 1f | >610 | 15/60 | 310/77 | 30/20 |
| 1g | >514 | 15/60 | 16/260 | 10/20 |
| 2a | 0.5 | 15/60 | 0.009–0.14 | 80–90 |
| 2b | 22 | 15 | 0.30 | 90 |
|  |  |  | 1.4 | 60 |
|  |  |  | 5.4 | 30 |
|  |  | 60 | 0.30–5.4 | 60–70 |
| 2c | 84 | 15/60 | 0.005–0.11 | 50–70 |
| 2d | 600 | 15/60 | 9.0 | 90/90 |
|  |  |  | 37 | 90/70 |
|  |  |  | 150 | 50/0 |
| 3b | >40 | 15/60 | 1.3/5.2 | 0/20 |
| 3c | >560 | 15/60 | 0.017–0.28 | 40–70/30–40 |
| 3d | >430 | 15/60 | 0.013–0.215 | 20–40/10–30 |
| 4a | >1240 | 15/60 | 0.2 | 50/90 |
|  |  |  | 0.6 | 80/100 |
|  |  |  | 2.3 | 80/80 |
| 4b | 42 | 15 | 0.65 | 90 |
|  |  |  | 2.7 | 90 |
|  |  |  | 11 | 40 |
| 4b |  | 60 | 0.65–11 | 70–80 |
| 5a | >670 | 15/60 | 18–290 | 70–100/20–70 |
| 5b | 380 | 15/60 | 0.6 | 40/20 |
|  |  |  | 24 | 100/30 |
|  |  |  | 96 | 100/100 |

[a]Compounds were tested at two different time intervals to allow for differences in bioavailability;
[b]Three different doses were tested, only one dose is recorded for inactive compounds.

TABLE IV

In Vivo Evaluation of Pyridinium Derivatives as Oral Pretreatment Agents Against GD in Mice.

| compd | $LD_{50}$ (μmol/kg) | time[a] (min) | dose[b] (μmol/kg) | % survival |
|---|---|---|---|---|
| 1b | 3600 | 30/120 | 60 | 30/70 |
| 1e | >3200 | 30/120 | 200 | 0/50 |
| 2a | 220 | 30/120 | 3.4 | 90/80 |
| 2b | 490 | 30/120 | 120 | 90/100 |
| 2c | 140 | 30/120 | 2.2 | 100/100 |
| 4b | 670 | 30/120 | 10 | 70/100 |
| 5a | 2900 | 30/120 | 730 | 40/50 |

[a]Compounds were tested at two different time intervals to allow for differences in bioavailability;
[b]Three different doses were tested, only one dose is recorded for inactive compounds.

TABLE V

In Vivo Evaluation of Pyridinium Derivatives as Reactivators Against GD in Mice.

| compd | $LD_{50}$ (μmol/kg) | dose[a] (μmol/kg) | % survival |
|---|---|---|---|
| 1a | 180 | 2.8 | 20 |

TABLE V-continued

In Vivo Evaluation of Pyridinium Derivatives as Reactivators Against GD in Mice.

| compd | $LD_{50}$ (μmol/kg) | dose[a] (μmol/kg) | % survival |
|---|---|---|---|
| 1b | >880 | 5.6 | 20 |
| 1d | >320 | 40 | 20 |
| 1e | >760 | 20 | 0 |
| 1f | >610 | 12 | 0 |
| 1g | >514 | 15 | 0 |
| 2a | 0.5 | 0.009–0.14 | 30–50 |
| 2b | 22 | 0.33 | 20 |
|  |  | 1.4 | 70 |
|  |  | 5.4 | 60 |
| 2c | 84 | 1.3 | 20 |
| 3a | >1100 | 27[b] | 50 |
|  |  | 110[b] | 70 |
|  |  | 430[b] | 90 |
|  |  | 6.8 | 20 |
|  |  | 54 | 0 |
|  |  | 430 | 70 |
| 3b | >40 | 1.3 | 10 |
| 3c | >560 | 0.28 | 10 |
| 3d | >430 | 0.215 | 20 |
| 4a | 9.6 | 0.2–2.3 | 0–50 |
| 4b | 42 | 0.65–11 | 30–50 |
| 5a | >670 | 18–290 | 70–90 |
| 5b | 380 | 6 | 20 |
|  |  | 24 | 40 |
|  |  | 96 | 90 |
| 2-PAMCl | 853 | 53 | 0 |
| HI-6 | 4500 | 280–1125 | 90–100 |

[a]Three different doses were tested, only one dose is recorded for inactive compounds.
[b]adjunct efficacy test, see text for details.

TABLE VI

In Vivo Evaluation of Pyridinium Derivatives as Reactivators Against GA in Mice.

| compd | $LD_{50}$ (μmol/kg) | dose (μmol/kg) | % survival[a] |
|---|---|---|---|
| 1c | >1970 | 30 | 0 |
| 1f | 2100 | 33 | 0 |
| 1g | >510 | 16 | 0 |
| 2a | 0.5 | 0.009 | 30 |
| 2c | 84 | 0.005 | 20 |
| 4a | 9.6 | 0.60 | 20 |
| 4b | 670 | 2.70 | 30 |
| 5a | >670 | 18 | 10 |
|  |  | 73 | 80 |
|  |  | 290 | 90 |
| 5b | 380 | 6 | 10 |
|  |  | 24 | 0 |
|  |  | 96 | 80 |

[a]Three different doses were tested, only one dose is recorded for inactive compounds.

What is claimed is:

1. A compound of the group consisting of the formulas:

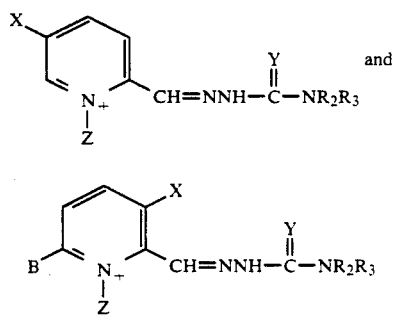

with any counterion to make pharmaceutically acceptable salts, wherein

Z is selected from the group consisting of $C_{1-6}$ alkyl, $C_{1-6}$ alkyl with an attached phenyl group, $C_{1-6}$ alkyl with an attached naphthyl group, $C_{1-6}$ alkyl with two attached phenyl groups, $C_{1-6}$ alkyl with an attached phenyl group mono, di or trisubstituted with J, $C_{1-6}$ alkyl with two attached phenyl groups mono, di or trisubstituted with J, $C_{1-6}$ alkyl with an attached naphthyl group mono, di, or trisubstituted with J, wherein J is selected from the group consisting of halogen, COOH, OH, CN, $NO_2$, $NH_2$, $C_{1-6}$ alkyl, $C_{1-6}$ alkoxy, $C_{1-6}$ alkylamine, $C_{1-6}$, alkyl-O-CO-, $C_{1-6}$ alkyl-O-CO-NH-, $C_{1-6}$ alkyl-NH—CO—NH-, $C_{1-6}$ alkyl-NH—CO—O—, $C_{1-6}$ alkyl NH—CO—, ($C_{1-6}$ alkyl)$_2$N-CO-, wherein X is selected from the group consisting of OH, $C_{1-6}$ alkyl-NH—CO—O—,($C_{1-6}$ alkyl)$_2$-N—CO—O, $C_{1-6}$ fluoroalkyl-NH—CO—O, ($C_{1-6}$ fluoroalkyl)$_2$-NH—CO—O, Y is O or S, wherein $R_2$ is selected from the group consisting of H, $C_{1-6}$ alkyl, phenyl, $C_{1-6}$ alkyl with an attached phenyl group, $C_{1-6}$ alkyl with an attached phenyl group mono, di, or trisubstituted with K, $C_{1-6}$ alkyl with an attached naphthyl group, $C_{1-6}$ alkyl with an attached naphthyl group mono, di, or trisubstituted with K, wherein $R_3$ is selected from the group consisting of H, $C_{1-6}$ alkyl, phenyl, $C_{1-6}$ alkyl with an attached phenyl group, $C_{1-6}$ alkyl with an attached phenyl group mono, di or trisubstituted with K, wherein K is selected from the group consisting of halogen, COOH, OH, CN, $NO_2$, $NH_2$, $C_{1-6}$ alkyl, $C_{1-6}$ alkoxy, $C_{1-6}$ alkylamine, $C_{1-6}$ alkyl-O-CO-, $C_{1-6}$ alkyl-O-CO-NH-, $C_{1-6}$ alkyl-NH—CO—NH—, $C_{1-6}$ alkyl-NH—CO—O—, $C_{1-6}$ alkyl NH—CO—, ($C_{1-6}$ alkyl)$_2$N-CO-, wherein B is selected from the group consisting of H, $C_{1-6}$ alkyl.

2. A compound of the group consisting of the formulas:

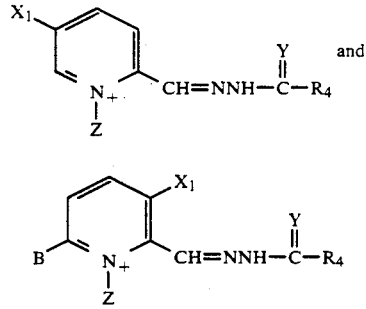

with any counterion to make pharmaceutically acceptable salts, wherein $X_1$ is selected from the group consisting of H, OH, $C_{1-6}$ alkyl-NH—CO—O—, ($C_{1-6}$ alkyl)$_2$-N—CO—O—, $C_{1-6}$ fluoroalkyl-NH—CO—O—, ($C_{1-6}$ fluoroalkyl)$_2$-NH—CO—O—, Y is O or S, Z is selected from the group consisting of $C_{1-6}$ alkyl, $C_{1-6}$ alkyl with an attached phenyl group, $C_{1-6}$ alkyl with an attached naphthyl group, $C_{1-6}$ alkyl with two attached phenyl groups, $C_{1-6}$ alkyl with an attached phenyl group mono, di or trisubstituted with J, $C_{1-6}$ alkyl with two attached phenyl groups mono, di or trisubstituted with J, $C_{1-6}$ alkyl with an attached naphthyl group mono, di, or trisubstituted with J, wherein J is selected from the group consisting of halogen, COOH, OH, CN, $NO_2$, $NH_2$, $C_{1-6}$ alkyl, $C_{1-6}$ alkoxy, $C_{1-6}$ alkylamine, $C_{1-6}$ alkyl-O-CO-, $C_{1-6}$ alkyl-O—CO—NH—, $C_{1-6}$ alkyl-NH—CO—NH—, $C_{1-6}$ alkyl-NH—CO—O—, $C_{1-6}$ alkyl NH—CO—, $(C_{1-6}$ alkyl$)_2$N-CO-, wherein $R_4$ is selected from the group consisting of $C_{1-6}$ alkyl with a pyridinium ring attached through nitrogen, $C_{1-6}$ alkyl with a pyridinium ring attached through nitrogen and mono, di, or trisubstituted with K, $C_{1-6}$ alkyl with a quinolinium ring attached through nitrogen and mono, di, or trisubstituted with K, $C_{1-6}$ alkyl with an isoquinolinium ring attached through nitrogen and mono, di, or trisubstituted with K, $C_{1-6}$ alkyl-T, wherein T is selected from the group consisting of formula (I) and formula (II),

Formula I

Formula II wherein R', R", and R''' are selected from the group consisting of H, $C_{1-6}$ alkyl, $C_{1-6}$ fluoroalkyl, $C_{1-6}$ alkyl with an attached phenyl group, $C_{1-6}$ alkyl with an attached phenyl group mono, di, or trisubstituted with K, $C_{1-6}$ fluoroalkyl with an attached phenyl group mono, di, or trisubstituted with K, wherein K is selected from the group consisting of halogen, COOH, OH, CN, $NO_2$, $NH_2$, $C_{1-6}$ alkoxy, $C_{1-6}$ alkylamine, $C_{1-6}$ alkyl-O-CO-, $C_{1-6}$ alkyl-O-CO-NH, $C_{1-6}$ alkyl -NH—CO—NH-, $C_{1-6}$ alkyl-NH-CO-O-, $C_{1-6}$ alkyl NH-CO-, $(C_{1-6}$ alkyl$)_2$N-CO, wherein B is selected from the group consisting of H, $C_{1-6}$ alkyl.

3. A compound of the formula:

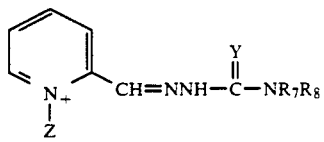

with any counterion to make pharmaceutically acceptable salts, wherein

Y is O or S,

Z is selected from the group consisting of $C_{1-6}$ alkyl, $C_{1-6}$ alkyl with an attached phenyl group, $C_{1-6}$ alkyl with an attached naphthyl group, $C_{1-6}$ alkyl with two attached phenyl groups, $C_{1-6}$ alkyl with an attached phenyl group mono, di, or trisubstituted with J, $C_{1-6}$ alkyl with two attached phenyl groups mono, dis or trisubstituted with J, $C_{1-6}$ alkyl with an attached naphthyl group mono, di, or trisubstituted with J, wherein J is selected from the group consisting of halogen, COOH, OH, CN, $NO_2$, $NH_2$, $C_{1-6}$ alkyl, $C_{1-6}$ alkoxy, $C_{1-6}$ alkylamine, $C_{1-6}$ alkyl-O—CO—, $C_{1-6}$ alkyl-O—CO—NH—, $C_{1-6}$ alkyl-NH—CO—NH—, $C_{1-6}$ alkyl -NH—CO—O—, $C_{1-6}$ alkyl NH—CO—, $(C_{1-6}$ alkyl$)_2$N-CO-, $R_7$ is selected from the group consisting of $C_{1-6}$ alkyl, phenyl, $C_{1-6}$ alkyl with an attached phenyl group, $C_{1-6}$ alkyl with an attached phenyl group mono, di, or trisubstituted with K, $C_{1-6}$ alkyl with an attached naphthyl group, $C_{1-6}$ alkyl with an attached naphthyl group mono, di, or trisubstituted with K, wherein $R_8$ is selected from the group consisting of $C_{1-6}$ alkyl, phenyl, $C_{1-6}$ with an attached phenyl group, $C_{1-6}$ alkyl with an attached phenyl group mono, di, or trisubstituted with K, wherein K is selected from the group consisting of halogen, COOH, OH, CN, $NO_2$, $NH_2$, $C_{1-6}$ alkyl, $C_{1-6}$ alkoxy, $C_{1-6}$ alkylamine, $C_{1-6}$ alkyl-O-CO-, $C_{1-6}$ alkyl-O-CO-NH-, $C_{1-6}$ alkyl-NH—CO—NH—, $C_{1-6}$ alkyl-NH—CO—O, $C_{1-6}$ alkyl NH—CO—, $(C_{1-6}$ alkyl$)_2$N-CO-.

* * * * *